US011583625B2

(12) United States Patent
Lee-Sepsick et al.

(10) Patent No.: US 11,583,625 B2
(45) Date of Patent: *Feb. 21, 2023

(54) METHODS AND DEVICES FOR MANAGING FLUID PRESSURE

(71) Applicant: Femasys, Inc., Suwannee, GA (US)

(72) Inventors: Kathy Lee-Sepsick, Suwanee, GA (US); Max S. Azevedo, Alpharetta, GA (US)

(73) Assignee: Femasys Inc., Suwanee, GA (US)

( * ) Notice: Subject to any disclaimer, the term of this patent is extended or adjusted under 35 U.S.C. 154(b) by 225 days.

This patent is subject to a terminal disclaimer.

(21) Appl. No.: 16/902,837

(22) Filed: Jun. 16, 2020

(65) Prior Publication Data

US 2020/0368424 A1 Nov. 26, 2020

Related U.S. Application Data

(63) Continuation of application No. 13/292,990, filed on Nov. 9, 2011, now Pat. No. 10,737,014.

(60) Provisional application No. 61/411,856, filed on Nov. 9, 2010.

(51) Int. Cl.
*A61B 6/00* (2006.01)
*A61B 8/08* (2006.01)
*A61M 5/00* (2006.01)

(52) U.S. Cl.
CPC ............... *A61M 5/00* (2013.01); *A61B 6/481* (2013.01); *A61B 8/481* (2013.01)

(58) Field of Classification Search
CPC .... A61M 5/00; A61M 5/1452; A61M 5/1407; A61M 5/007; A61M 31/005; A61B 6/481; A61B 8/481
See application file for complete search history.

(56) References Cited

U.S. PATENT DOCUMENTS

| 6,450,963 | B1* | 9/2002 | Ackerman | ............ | A61B 8/481 |
| | | | | | 600/463 |
| 9,554,826 | B2 | 1/2017 | Lee-Sepsick et al. | | |
| 10,172,643 | B2* | 1/2019 | Lee-Sepsick | ....... | A61M 5/1452 |
| 10,737,014 | B2* | 8/2020 | Lee-Sepsick | ........... | A61M 5/00 |
| 2009/0127288 | A1* | 5/2009 | Keller | ............... | B05C 17/00579 |
| | | | | | 222/1 |

FOREIGN PATENT DOCUMENTS

| CA | 2817330 | 11/2011 |
| EP | 263780 | 11/2011 |
| EP | 3178422 | 11/2011 |

(Continued)

OTHER PUBLICATIONS

Pasic et al., "A Practical Manual of Hysteroscopy and endometrial ablation techniques" 2004, Taylor & Francis, 278 pages (Year: 2004).*

(Continued)

*Primary Examiner* — Boniface Ngathi N
(74) *Attorney, Agent, or Firm* — Mary Anthony Merchant

(57) ABSTRACT

The present invention comprises methods, compositions, devices and systems for determining the status of, or treating, a body structure or conduit. An embodiment of the invention comprises a fluid pressure control device for pressure control of fluid introduced into a body structure or conduit.

19 Claims, 16 Drawing Sheets

(56) References Cited

FOREIGN PATENT DOCUMENTS

| JP | 6259660 | 11/2011 | | |
|----|---------|---------|---|---|
| WO | WO-2010036721 A2 | * | 4/2010 | ............. A61B 1/303 |

OTHER PUBLICATIONS

NonFinal Office Action, dated Mar. 27, 2013, in U.S. Appl. No. 13/292,990, filed Sep. 11, 2011, Applicant Femasys Inc., 10 p.
Response to NonFinal Office Action, dated Aug. 27, 2013, in U.S. Appl. No. 13/292,990, filed Sep. 11, 2011, Applicant Femasys Inc., 11 p.
Final Office Action, dated Sep. 12, 2013, in U.S. Appl. No. 13/292,990, filed Sep. 11, 2011, Applicant Femasys Inc., 11' p.
Response to Final Office Action, dated Dec. 12, 2013, in U.S. Appl. No. 13/292,990, filed Sep. 11, 2011, Applicant Femasys Inc., 15 p.
NonFinal Office Action, dated Sep. 18, 2014, in U.S. Appl. No. 13/292,990, filed Sep. 11, 2011, Applicant Femasys Inc., 11 p.
Response to NonFinal Office Action, dated Mar. 18, 2015, in U.S. Appl. No. 13/292,990, filed Sep. 11, 2011, Applicant Femasys Inc., 12 p.
Final Office Action, dated Jul. 16, 2015, in U.S. Appl. No. 13/292,990, filed Sep. 11, 2011, Applicant Femasys Inc., 12 p.
Response to Final Office Action, dated Oct. 16, 2015, in U.S. Appl. No. 13/292,990, filed Sep. 11, 2011, Applicant Femasys Inc., 13 p.
Request for Continued Examination, dated Nov. 16, 2015, in U.S. Appl. No. 13/292,990, filed Sep. 11, 2011, Applicant Femasys Inc., 16 p.
NonFinal Office Action, dated Apr. 21, 2016, in U.S. Appl. No. 13/292,990, filed Sep. 11, 2011, Applicant Femasys Inc., 15 p.
Response to NonFinal Office Action, dated Aug. 22, 2016, in U.S. Appl. No. 13/292,990, filed Sep. 11, 2011, Applicant Femasys Inc., 12 p.
Final Office Action, dated Dec. 9, 2016, in U.S. Appl. No. 13/292,990, filed Sep. 11, 2011, Applicant Femasys Inc., 17 p.
Response to Final Office Action, dated Feb. 9, 2017, in U.S. Appl. No. 13/292,990, filed Sep. 11, 2011, Applicant Femasys Inc., 15 p.
Advisory Action, dated Mar. 20, 2017, in U.S. Appl. No. 13/292,990, filed Sep. 11, 2011, Applicant Femasys Inc., 4 p.
Request for Continued Examination, dated May 9, 2017, in U.S. Appl. No. 13/292,990, filed Sep. 11, 2011, Applicant Femasys Inc., 15 p.
NonFinal Office Action, dated Oct. 5, 2017 in U.S. Appl. No. 13/292,990, filed Sep. 11, 2011, Applicant Femasys Inc., 14 p.
Response to NonFinal Office Action, dated Feb. 5, 2018, in U.S. Appl. No. 13/292,990, filed Sep. 11, 2011, Applicant Femasys Inc., 14 p.
Notice of NonCompliant Response, dated Sep. 20, 2018, in U.S. Appl. No. 13/292,990, filed Sep. 11, 2011, Applicant Femasys Inc., 3 p.
Response to NonFinal Office Action, dated Oct. 15, 2018, in U.S. Appl. No. 13/292,990, filed Sep. 11, 2011, Applicant Femasys Inc., 7 p.
Final Office Action, dated Nov. 14, 2019, in U.S. Appl. No. 13/292,990, filed Sep. 11, 2011, Applicant Femasys Inc., 18 p.
Response to Final Office Action, dated Feb. 14, 2020, in U.S. Appl. No. 13/292,990, filed Sep. 11, 2011, Applicant Femasys Inc., 7 p.
NonFinal Office Action, dated Mar. 17, 2020, in U.S. Appl. No. 13/292,990, filed Sep. 11, 2011, Applicant Femasys Inc., 11 p.
Response to NonFinal Office Action, dated Oct. 104, 2020, in U.S. Appl. No. 13/292,990, filed Sep. 11, 2011, Applicant Femasys Inc., 11 p.
Notice of Allowance, dated Apr. 21, 2020, in U.S. Appl. No. 13/292,990, filed Sep. 11, 2011, Applicant Femasys Inc., 9 p.
Office Action, dated Sep. 6, 2017, for Canadian patent application No. 2817330, filed Nov. 9, 2011, Applicant: Femasys Inc.; (4 pages).
First Notice of Allowance, dated May 15, 2018, for Canadian patent application No. 2817330, filed Nov. 9, 2011, Applicant: Femasys Inc.; (4 pages).
Second Notice of Allowance, dated Jan. 3, 2019, for Canadian patent application No. 2817330, filed Nov. 9, 2011, Applicant: Femasys Inc.; (1 pages).
Supplemental Search Report and Opinion, dated May 8, 2014, for European patent application No. EP 263780, filed Nov. 9, 2011, Applicant: Femasys Inc.; (5 pages).
Office Action, dated Jun. 18, 2014, for European patent application No. EP 263780, filed Nov. 9, 2011, Applicant: Femasys Inc.; (4 pages).
Decision to Grant, dated Jan. 5, 2017, for European patent application No. EP 263780, filed Nov. 9, 2011, Applicant: Femasys Inc.; (2 pages).
Supplemental Search Report and Opinion, dated May 2, 2017, for European patent application No. EP 3178422, priority to Nov. 9, 2011, Applicant: Femasys Inc.; (6 pages).
Office Action, dated Mar. 1, 2018, for European patent application No. EP 3178422, priority to Nov. 9, 2011, Applicant: Femasys Inc.; (4 pages).
Decision to Grant, dated Dec. 18, 2018, for European patent application No. EP 3178422, priority to Nov. 9, 2011, Applicant: Femasys Inc.; (5 pages).
First Office Action, dated Sep. 30, 2015, for Japanese patent application No. 6259660, filed Nov. 9, 2011, Applicant: Femasys Inc.; (4 pages).
Second Office Action, dated Jul. 29, 2016, for Japanese patent application No. 6259660, filed Nov. 9, 2011, Applicant: Femasys Inc.; (3 pages).
Third Office Action, dated Jul. 27, 2017, for Japanese patent application No. 6259660, filed Nov. 9, 2011, Applicant: Femasys Inc.; (2 pages).
Decision to Grant, dated Nov. 16, 2017, for Japanese patent application No. 6259660, filed Nov. 9, 2011, Applicant: Femasys Inc.; (3 pages).

* cited by examiner

METHODS AND DEVICES FOR MANAGING FLUID PRESSURE

RELATED APPLICATIONS

The present disclosure is a continuation application of U.S. patent application Ser. No. 13/292,990, now U.S. Pat. No. 10,737,014, which claims the benefit of priority of U.S. Provisional Patent Application Ser. No. 61/411,856, filed Nov. 9, 2010, each of which is herein incorporated in its entirety.

FIELD OF THE INVENTION

This invention is directed to methods and devices for managing pressure of a fluid while providing the fluid to a body, for example during hysterosalpingography.

BACKGROUND

Women who undergo a permanent sterilization procedure rendering their fallopian tubes blocked by numerous means, including but not limited to coils, implants, agents creating an occluded lumen, ablation of the lumen, and the like, require a post-procedure confirmatory test that the procedure was successful. Typically, the confirmatory test is performed at 3 months post-procedure but can also be repeated if the first findings are unsatisfactory or inconclusive. Current confirmatory methods involve a type of hysterosalpingogram (HSG), where a contrast dye study is performed under fluoroscopic guidance. The confirmatory test (referred to herein as "confirmatory HSG") requires that the physician use a much lower fluid pressure than a traditional HSG study because the physician must avoid expulsion, dislodgement, or disruption of the occlusion. If too great a pressure is applied, then a successful sterilization procedure can be negated or the uterus and/or fallopian tubes may be harmed or damaged. There is no currently available method or device for physicians to use that indicates the fluid pressure or where the fluid pressure is controlled.

Current confirmatory HSG testing procedures to ensure that fallopian tubal occlusion has occurred are challenging and tedious for physicians to execute. Physicians are required to remain below an established safe operating pressure, accepted by the Food and Drug Administration (FDA) as 200 mm Hg, but there is no device currently available to ensure this level of pressure is not exceed. The current method of confirming closure of fallopian tubes and the devices available do not provide a satisfactory approach and provide neither a high level of assurance nor a real-time indication of the pressure created by the fluid contained in the uterus due to the blocked fallopian tubes.

Current methods also are inconvenient for patients. The patient is instructed to use an alternative form of contraception for the first three months following the initial fallopian tube occlusion procedure. When the confirmatory HSG is performed to evaluate fallopian tube occlusion, and only if there is evidence of bilateral occlusion of the tubes, the physician may instruct the patient to discontinue the use of alternative contraception and rely entirely on the occlusion procedure. If the confirmatory HSG does not demonstrate tubal occlusion, or shows tubal patency beyond the occlusive device or means or if the results are inconclusive, the patient must continue the use of alternative contraception for three additional months and repeat the confirmatory HSG at six months post-procedure. If tubal occlusion is not established at six months, the patient must be advised not to rely on the permanent sterilization occlusive method for contraception. This may cause the patient to undergo a second occlusion procedure. In addition, there are serious and possibly life threatening consequences to advising a patient that she can rely on the tubal occlusive method if the assessment is inaccurate and the fallopian tubes are not fully occluded.

Given the importance of the confirmatory HSG test in providing assurance of a successful permanent sterilization procedure, there is a need for improved methods and devices that will enable physicians to make better, and more accurate, diagnoses. In particular, there is a need for methods and devices that enable a physician to carry out the confirmatory HSG test without fear of expulsing, disrupting or dislodging the occlusion created or delivered. Devices that will allow the physician to achieve a more accurate result or diagnosis will bring not only peace of mind to the patient but to the physician rendering the diagnosis.

SUMMARY

The present invention comprises methods, systems and compositions for providing pressure-regulated control of fluids, for example, during confirmatory hysterosalpingogram or standard hysterosalpingogram, for example, performed fluroscopically or sonographically. The present invention comprises methods, systems and compositions for providing fluid to a body structure or organ; containing the fluids within the body structure for a period of time, or ceasing to provide fluid if the maximum desired fluid pressure is reached; providing an indication of pressure reached during fluid dispensing; and controlling the flow of fluids to to the body structure to prevent the user from inadvertently exerting excess force to the body structure or cavity. In an aspect, the invention comprises devices for pressure-regulated control of contrast media for imaging one or more body structures, such as the uterus and/or fallopian tubes. In an aspect, methods of the present invention comprise providing fluids to a body duct or cavity, for fluoroscopic or ultrasound imaging of body ducts and cavities, such as altered body ducts and cavities, wherein the fluid pressure of the fluoroscopic or ultrasound contrast media may be monitored and/or controlled during the provision of the contrast media. While confirmatory HSG and standard HSG is disclosed herein, it is contemplated that the present invention is not limited to only this application, and the devices and systems disclosed herein may be employed in applications where fluid pressure regulation for treatment of human or animals, or inanimate objects, is desired.

In accordance with the purposes of the invention, as embodied and broadly described herein, the invention comprises methods and devices intended to provide pressure management of a fluid delivered to a cavity or duct, for example, for treatment or for fluoroscopic or sonographic imaging of the cavity and/or duct.

The invention comprises fluid pressure control devices and systems. The invention comprises constant force spring fluid pressure control delivery devices and systems comprising a constant force spring fluid pressure control device. The invention comprises check-valve fluid pressure control devices and systems comprising a check-valve fluid pressure control device.

The invention comprises methods of using a fluid pressure control device and system for determining the patency of a biological cavity or duct. The invention comprises methods comprising fluid pressure control devices and systems for determining if one or more fallopian tubes are occluded. The invention comprises methods comprising fluid pressure control devices and systems for treating altered or unaltered organs, cavities, ducts, conduits, passageways and other body structures accessed by such.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURES

The accompanying figures, which are incorporated in and constitute a part of this specification, illustrate several aspects and together with the description serve to explain the principles of the invention.

Figure 1:
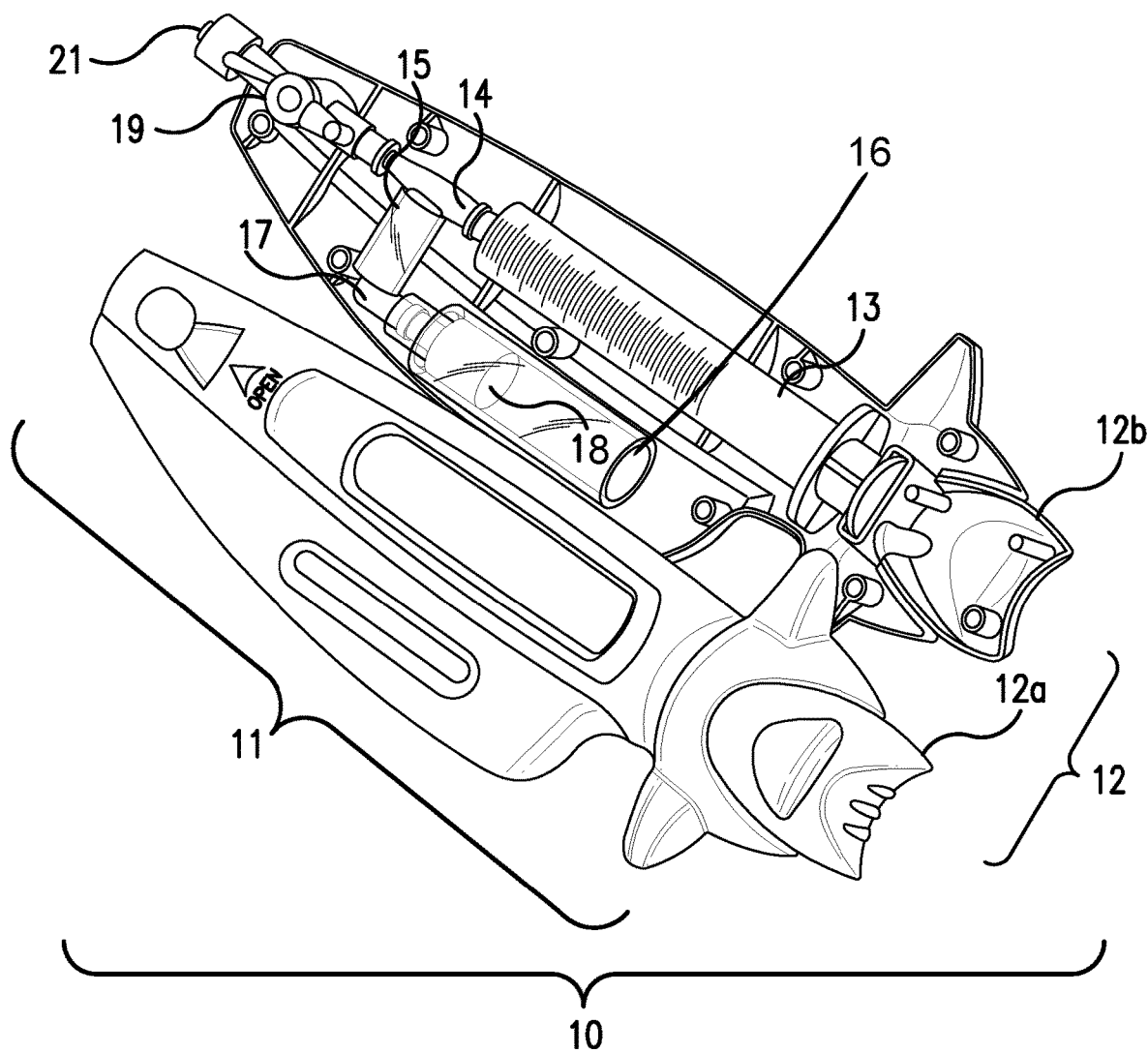
FIG. 1 shows an exemplary fluid pressure control device.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention comprises methods, systems and devices useful for determining the status of a body conduit or cavity under controlled conditions, for example, where the pressure of a fluid, used, for example, in fluoroscopy or sonography, is kept at or below a determined pressure. The present invention comprises methods, systems and devices useful for providing a fluid to a body organ, conduit or cavity under controlled fluid pressure conditions, for example, where the pressure of a liquid, used, for example, in treating an altered organ, is kept at or below a predetermined pressure. For example, the present invention comprises methods, systems and devices for use in determining the extent of occlusion of one or more fallopian tubes following a fallopian tube occlusion procedure. In an aspect of the invention, methods, devices and systems comprise determining the occlusion or patency of one or more fallopian tubes by providing a visualizable fluid to the uterus of a female mammal wherein the pressure of the fluid provided does not exceed a desired pressure. In an aspect of the invention, methods, devices and systems comprise treating one or more fallopian tubes by providing a fluid to the uterus and at least one fallopian of a female mammal wherein the pressure of the fluid provided does not exceed a desired pressure. For example, a fluid may be provided to a uterus and/or at least one fallopian tube, wherein the pressure of the fluid equals but does not exceed 1,000 mm Hg, 900 mm Hg, 800 mm Hg, 700 mm Hg, 600 mm Hg, 500 mm Hg, 400 mm Hg, 350 mm Hg, 300 mm Hg, 250 mm Hg, 200 mm Hg, 150 mm Hg, 100 mm Hg, 75 mm Hg, 50 mm Hg, or 25 mm Hg, or levels thereinbetween. Devices and systems disclosed herein may comprise at least a syringe or containment device for the delivery of a fluid.

In an aspect, methods, systems and devices of the present invention provide pressure management of a fluid delivered to a cavity, conduit or duct wherein the fluid, may be a liquid, gas or combination of liquid and gas. For example, a fluid may be visualizable in fluoroscopic or sonographic imaging methods. For example, a fluid may be a treatment fluid. In an aspect, an imaging method of the present invention comprises determining the status of a cavity, conduit or a passageway in the body, such as an altered cavity, conduit or a passageway in the body, by providing a contrast medium fluid to the cavity, conduit or a passageway using a device or system disclosed herein, and thereby controlling the fluid pressure of the contrast medium fluid. In an aspect, a passageway that is evaluated is a fallopian tube and a cavity may be a uterine cavity of a female mammal. In an aspect, a treatment method of the present invention comprises treating an altered cavity, conduit or a passageway in the body by providing a treatment fluid using a device or system disclosed herein, and thereby controlling the fluid pressure of the treatment fluid.

Methods of the present invention comprise use of fluid pressure control devices and systems described herein to provide controlled delivery of a fluid to a biological cavity, where the fluid pressure control device limits the pressure of fluid in the cavity to a desired pressure, for example, such as about 200 mm Hg or less, and optionally, provides feedback, such as information or an indication, to the operator regarding the fluid pressure in the cavity. Disclosed herein are devices, systems and compositions used in methods for determining the status of a cavity, for example, a uterus, and/or a conduit, for example at least one fallopian tube, in a mammal, after one or more of the organ, cavity or a conduit is altered or where the organ, cavity or a conduit is not altered. Disclosed herein are devices, systems and compositions used in methods for treating a cavity, for example, a uterus, and/or a conduit, for example at least one fallopian tube, in a mammal, after one or more of the organ, cavity or a conduit is altered or where the organ, cavity or a conduit is not altered. It is contemplated that the invention is not to be limited by this example, and that those skilled in the art can employ the invention for other determinations of the status of other cavities, conduits or passageways.

A common medical procedure for imaging the uterus and fallopian tubes of a normal patient, one who does not have altered organs, is hysterosalpingography. In general, such procedures rely on injecting contrast media into the uterus and fallopian tubes using a uterine access catheter and one or more elements for maintaining the media in the uterus, such as by having an elastomeric balloon near the catheter distal end for sealing against the internal cervical os within the uterus. The anatomical structures of the uterus and fallopian tubes are then fluoroscopically or sonographically imaged in a conventional manner. The status of the uterus and the fallopian tubes is visualized by a medical professional. If the fallopian tubes are patent, the contrast media flows into the uterus and out of the fallopian tubes, and the flow out of one or more fallopian tubes is visualized. There is generally, little or no fluid pressure increase in the uterus by the injection of the contrast medium because the fluid can flow out an exit of at least one fallopian tube.

If the fallopian tubes are not patent, no fluid flow out of the fallopian tube(s) is seen, and fluid pressure increases in the uterus as the exits (fallopian tubes) are blocked. Currently, in normal patients without altered body structures, the fluid pressure increase is not deemed harmful to the normal patient, and the fluid pressure increase in the uterus/fallopian tubes is not controlled even though it causes pain or discomfort. Devices, systems and methods of the present invention may be used for normal patients to provide imaging procedures and/or treatments that have reduced or no pain. Women that undergo an evaluation of their fallopian tubes to determine if they are patent benefit from reasonable, controlled pressure levels being used in providing fluids, and use of controlled fluid pressures substantially eliminates discomfort and the occurrence of a vasovagal response. Sufficiently applied fluid pressure is beneficial for treatments of fallopian tube(s) in that mucous or a naturally occurring blockage may be "flushed" or moved from the tube to create a patency, however, excessive fluid pressures are unnecessary for any patient, and can make a patient highly uncomfortable and sick during or after the procedure. The present invention comprises a method for enhancing fertility comprising providing fluid using a fluid pressure control device to provide fluid below a predetermined pressure level to one or more fallopian tube(s) of a mammal, such as a human or animal. A method of reducing pain during treatment or imagining of a uterus and/or at least one fallopian tube, comprising providing fluid using a fluid pressure control device to provide fluid below a predetermined pressure level to one or more fallopian tube(s) of a mammal, such as a human or animal.

Once the status of the uterus/fallopian tubes is determined, the balloon at the internal cervical os, or other element(s) used, is released and the fluid is allowed to flow out of the uterus through the cervix.

When a uterus and/or at least one fallopian tube is altered, for example, by surgery, trauma, occluding, blocking or severing one or more fallopian tubes, or by reattaching or opening one or more fallopian tubes, a normal hysterosalpingography procedure may provide fluid to the body structures, the uterus and at least the opening of a fallopian tube, at a fluid pressure level that may damage the altered organs, because the fluid pressure of the contrast medium is not the same as in a normal patient, due to, for example, restricted fluid flow, and the increased fluid pressure may dislodge implanted structures or ingrowth by cells or tissues, or may disrupt or tear sutures or other attachments in the uterus and/or fallopian tube(s). Determining the status of an altered uterus, such as after surgery, trauma, removal of polyps, or reconstruction, may require a controlled fluid pressure procedure, wherein the fluid pressure of the contrast medium used to visualize the status of the altered uterus must be kept a particular level or below that level to prevent damage to the altered uterus. A procedure to assess the status of an organ, such as an altered uterus and/or fallopian tube, after a procedure such as surgery or other medical procedure, is referred to herein as a confirmatory procedure. A confirmatory HSG may be performed after a surgical or other medical procedure has been performed on a uterus and/or at least one fallopian tube.

As many body structures are contained within the body and are not visible from the exterior, medical personnel can only determine the status of an altered organ, such as a repaired uterus or closure of the fallopian tubes, by external visualizable methods. The present invention comprises devices, systems and compositions for confirmatory HSG that provide a visualizable fluid to determine the status of the uterus and/or fallopian tubes at a controlled fluid pressure level, and optionally, at a fluid pressure level that is lower than that of the fluid pressure levels used in an HSG performed on normal patients with unaltered organs. The present invention comprises devices, systems and compositions for procedures that provide a visualizable fluid to determine the status of an altered uterus and/or fallopian tube(s) at a controlled fluid pressure level, and optionally, at a fluid pressure level that is lower than that of the fluid pressure levels used in the procedure when performed on normal patients with unaltered organs. The present invention is useful for procedures where a medical professional needs to avoid expulsion, dislodgement, or disruption of an organ, a conduit, an occlusion, a surgical repair, or other alterations to an organ, conduit or passageway. For example, if too great a fluid pressure is applied to one or more fallopian tubes that have been occluded, then a successful sterilization procedure may be negated or the uterus and/or fallopian tubes may be harmed or damaged.

As used herein an altered organ, conduit or other body structure refers to an organ, conduit or other body structure that has undergone one or more of a surgical procedure, a medical procedure or a trauma that has changed the physical structure of the organ, conduit or other body structure from the physical structure as it existed immediately prior to the surgical procedure, medical procedure or trauma. In an aspect, the altered body structure is at least one fallopian tube wherein at least one fallopian tube has undergone a medical or surgical procedure to occlude, block, place a plug or other structure in one or more fallopian tubes, or to sever the fallopian tube. An aspect of the present invention contemplates that the altered status of the organ or body structure is due to actions taken with the purpose of altering the organ or body structure. The present invention is useful for medical procedures for normal, not altered body structures and altered body structures.

A method of the present invention comprises determining the status of an altered body structure, such as by visualization techniques of sonography or fluorography, comprising, providing, to an altered body structure, a contrast medium by use of a controlled delivery device for regulated pressure control of the contrast medium, wherein the device comprises at least a first container for a fluid in fluid connection with an exit port; a pressure relief valve, wherein the pressure relief valve is in fluid connection between the exit port and the first container; optionally, a second container in fluid connection with the pressure relief value such that when the valve opens, fluid flows into the second container; an element for moving fluid from the first container to the exit port. The device may further comprise a contrast medium contained by the first container, or a step may comprise providing a contrast medium to the first container, referred to as charging or filling the container, or providing pre-filled first containers that may be placed in fluid connection with the rest of the device as if it was an original first container.

By moving fluid from the first container to the exit port, the contrast medium fluid moves from the first container, out the exit port, optionally through a catheter, and enters a body structure, and while the fluid is moving, the fluid pressure of the contrast medium fluid is maintained at a level at or lower than a predetermined level. Once an effective amount of the fluid has been provided at the desired pressure to one or more body structures, the fluid flow may be stopped, and/or other procedures may ensue. For example, a method comprises providing an effective amount of a contrast medium fluid to an altered uterus and/or fallopian tubes and then visualization techniques may be performed for visualization of the contrast media in the altered uterus and/or fallopian tubes and determination of the status of the organs.

A method of the present invention comprises treating an altered body structure, such as by providing a treatment composition to an altered body structure, comprising, providing, to an altered body structure, a treatment fluid by use of a fluid pressure control device for regulated pressure control of the treatment fluid, wherein the device comprises at least a first container for a fluid in fluid connection with an exit port; a pressure relief valve, wherein the pressure relief valve is in fluid connection between the exit port and the first container; optionally, a second container in fluid connection with the pressure relief value such that when the valve opens, fluid flows into the second container; an element for moving fluid from the first container to the exit port. The device may further comprise a treatment fluid contained by the first container, or a step may comprise providing a treatment fluid to the first container. The device may further comprise a treatment composition contained by the first container, or a step may comprise providing a treatment composition to the first container, referred to as charging or filling the container, or providing pre-filled first containers that may be placed in fluid connection with the rest of the device as if it were an original first container.

By moving fluid from the first container to the exit port, the treatment fluid moves from the first container, out the exit port, optionally through a catheter, and enters a body structure, and while the fluid is moving, the fluid pressure of the treatment fluid is maintained at a level at or lower than a predetermined level. Once an effective amount of the fluid has been provided at the desired pressure to one or more body structures, the fluid flow may be stopped, and/or other procedures may ensue. For example, a method comprises providing an effective amount of a treatment fluid to an altered uterus and/or fallopian tubes and allowing the treatment fluid to remain in contact with the altered uterus and/or fallopian tubes. The treatment fluid may be released from contact with the altered uterus and/or fallopian tubes for example, by allowing the treatment fluid to exit through the cervix.

A method of the present invention comprises determining the status of a body structure, for example, an organ, cavity or a conduit, such as by visualization techniques of sonography or fluorography, comprising, providing, to a body structure, a contrast medium by use of a fluid pressure control device for regulated pressure control of the contrast medium, wherein the device comprises at least a first container for a fluid in fluid connection with an exit port; a pressure relief valve, wherein the pressure relief valve is in fluid connection between the exit port and the first container; optionally, a second container in fluid connection with the pressure relief value such that when the valve opens, fluid flows into the second container; an element for moving fluid from the first container to the exit port. The device may further comprise a contrast medium contained by the first container, or a step may comprise providing a contrast medium to the first container, referred to as charging or filling the container, or providing pre-filled first containers that may be placed in fluid connection with the rest of the device as if it was an original first container.

By moving fluid from the first container to the exit port, the contrast medium fluid moves from the first container, out the exit port, optionally through a catheter, and enters a body structure, and while the fluid is moving, the fluid pressure of the contrast medium fluid is maintained at a level at or lower than a predetermined level. Once an effective amount of the fluid has been provided at the desired pressure to one or more body structures, the fluid flow may be stopped, and/or other procedures may ensue. For example, a method comprises providing an effective amount of a contrast medium fluid to a normal uterus and/or fallopian tubes and then visualization techniques may be performed for visualization of the contrast media in the uterus and/or fallopian tubes, for example for determination of the status of the organs.

A method of the present invention comprises treating a body structure, for example, an organ, cavity or a conduit, such as by providing a treatment composition to a body structure, comprising, providing, to a body structure, a treatment fluid by use of a fluid pressure control device for regulated pressure control of the treatment fluid, wherein the device comprises at least a first container for a fluid in fluid connection with an exit port; a pressure relief valve, wherein the pressure relief valve is in fluid connection between the exit port and the first container; optionally, a second container in fluid connection with the pressure relief value such that when the valve opens, fluid flows into the second container; an element for moving fluid from the first container to the exit port. The device may further comprise a treatment fluid contained by the first container, or a step may comprise providing a treatment fluid to the first container. The device may further comprise a treatment composition contained by the first container, or a step may comprise providing a treatment composition to the first container, referred to as charging or filling the container, or providing pre-filled first containers that may be placed in fluid connection with the rest of the device as if it were an original first container.

By moving fluid from the first container to the exit port, the treatment fluid moves from the first container, out the exit port, optionally through a catheter, and enters a body structure, and while the fluid is moving, the fluid pressure of the treatment fluid is maintained at a level at or lower than a predetermined level. Once an effective amount of the fluid has been provided at the desired pressure to one or more body structures, the fluid flow may be stopped, and/or other procedures may ensue. For example, a method comprises providing an effective amount of a treatment fluid to a normal uterus and/or fallopian tubes and allowing the treatment fluid to remain in contact with the uterus and/or fallopian tubes. The treatment fluid may be released from contact with the uterus and/or fallopian tubes for example, by allowing the treatment fluid to exit through the cervix.

During the providing of a fluid to an altered organ, cavity or a conduit, or to an unaltered normal organ, cavity or a conduit, should the fluid pressure of the fluid rise above or be greater than the predetermined or desired pressure level, a one-way pressure relief valve will open, and fluid is diverted out of the device and/or into a second container, which stops the flow of fluid from the first container and out the exit port, until the pressure drops below the predetermined or desired pressure level, at which point the relief valve relaxes to its closed position, permitting flow. A stopcock valve may be placed in fluid connection between the exit port and the relief valve. When providing fluid, the stopcock valve or other controllable open/close fluid line valve, is in an open position so that fluid flows out the exit port. When the relief valve opens, the stopcock valve may be closed to prevent retrograde fluid flow into the exit port. The stopcock valve may be closed when a sufficient amount of fluid has been provided to the altered organ to maintain fluid within the system (catheter and fluid pressure control device) to allow for other procedures, such as visualization of the body structure, or contact of treatment fluid with the body structure.

An altered body structure may be at least one occluded fallopian tube of a mammal, or an altered body structure may be a uterus of a mammal. Visualization techniques include, but are not limited to, sonography and fluorography. Treatment fluids may comprise any fluid provided to an organ, cavity, conduit or passageway that may provide a benefit to the organ, cavity, conduit or passageway. The pressure relief valve may open at a predetermined fluid pressure, wherein the fluid pressure may be at 1,000 mm Hg or at a lower pressure, including but not limited to, 900 mm Hg, 800 mm Hg, 700 mm Hg, 600 mm Hg, 500 mm Hg, 400 mm Hg, 350 mm Hg, 300 mm Hg, 250 mm Hg, 200 mm Hg, 150 mm Hg, 100 mm Hg, 75 mm Hg, 50 mm Hg, or 25 mm Hg, or levels thereinbetween. For compatibility with current US FDA regulations, the pressure relief valve may open when the fluid pressure exceeds 200 mm Hg.

A method of the present invention may comprise one or more pretreatment steps that occur prior to providing a fluid at a controlled fluid pressure. For example, a pretreatment step may comprise providing an antiseptic solution to the cervix. An aspect of the present invention comprises a method comprising inserting a catheter into and through the cervix and into the uterus, wherein the catheter is in communication with a fluid pressure control device as described herein. The catheter may comprise an element for preventing fluid flow out of the cervix. Such elements are known in the art and included, but are not limited to, an elastomeric balloon near the catheter's distal end, which when inflated, seals against the internal cervical os within the cervix, and blocks fluid flow from the uterus. A fluid, such as a treatment fluid or contrast media, is dispensed from a fluid pressure control device of the present invention, through the catheter into the uterus and the fluid pressure maximum is maintained at or below about 200 mm Hg. The fluid pressure control device insures that the fluid pressure in the uterus is controlled and maintained at or below the desired limit. Fluoroscopic X-ray or sonographic images are taken or viewed at various points of the procedure, when the fluid is a contrast medium, or in procedures where such visualization is desired.

The present invention comprises fluid pressure control devices and systems. A device of the present invention comprises at least a first container for a fluid, in fluid connection with an exit port; a pressure relief valve, wherein the pressure relief valve is in fluid connection with the exit port and the first container, and is located between the exit port and the first container; optionally, a second container in fluid connection with the pressure relief value such that when the valve opens, fluid flows in one direction to the second container; an element for moving fluid from the first container to the exit port. The device may further comprise a fluid contained by the first container, or may comprise a first container comprising a contained fluid. A system of the present invention may comprise a fluid pressure control device, a catheter that attaches to an attachment element of the exit port, connection elements, a second catheter for fluid diverted by the relief valve, other devices, including devices disclosed herein for providing compositions directly to fallopian tubes or devices for generating and/or providing contrast media, such as saline and air.

A fluid pressure control device 10 is shown in FIG. 1. 11 is a top housing for device 10, and may or may not be present, and may vary from this design. 12a and 12b are each half of plunger knob 12, and when, for example, housing 11 is in place, 12a and 12b form plunger knob 12. Not shown in FIG. 1 is the plunger body which slidably resides within first container 13 and the plunger body is attached on its proximal end to plunger knob 12, and on its distal end, has a fluid seal element so that fluid is contained by the container 13 and the distal surface of the fluid seal element. Cylinders such as syringes, and syringe plungers are known in the art. As shown in FIG. 1, the plunger body is completely extended through first container 13. As the plunger knob is pulled in a proximal direction, away from container 13, the attached plunger body slides though the interior of container 13, moving the fluid seal element in a distal to proximal direction (from left to right in FIG. 1), and expanding the area for containing a fluid within first container 13.

First container 13 is connected to pressure relief valve 14, and first container 13 may be connected directly to pressure relief valve 14 by connection elements, or there may be tubing connecting first container 13 to pressure relief valve 14. Pressure relief valve 14 is also connected to tubing 15, which may exit the device, or may be in fluid connection with second container 16. Pressure relief valve 14 may be connected to second container 16 by elbow connection 17, or other fluid connection elements. Within second container 16 is indicating element 18, which may be a fluid seal or other movable, lightly resistive to movement element that contains fluid on its distal surface and is pushed through the second container in a proximal direction by the fluid pressure, but indicating element 18 creates little to no resistive pressure on the fluid. Indicating element 18 allows the user to see that fluid has exited into the containment area, i.e. that the pressure relief valve was opened. For example, indicating element 18 may be colored, or glow in the dark so it is easier to visualize. Indicating element 18 contains the fluids exiting through the relief valve in the second container and moves in a proximal direction as more fluid enters the second container and when the entire chamber is filled, indicating element 18 may fall out of the proximal end opening of second container so there is no rise in pressure. As shown in FIG. 1, second container 16 is open on its proximal end. Indicating element 18 has very low resistance to moving so it does not affect pressure. Pressure relief valve 14 is connected on its proximal end to stopcock valve 19 having a handle 20. Pressure relief valve 14 may be connected directly to stopcock valve 19 by connection elements, or there may be tubing connecting pressure relief valve 14 to stopcock valve 19. Exit port 21 may comprise attachment elements, such as male or female luer lock elements, or other attachment elements that connect the fluid pressure device 10 to a catheter or other devices (not shown).

To provide fluid from a fluid pressure control device, when container 13 contains fluid, and the plunger body, fluid seal element and plunger knob are at a proximal location, such as placing the fluid seal element near the proximal end of container 13, plunger knob 12 is moved from a proximal location to a more distal location. Slidable movement of the plunger body with the fluid seal element moves liquid from first container 13 through at least pressure relief valve 14, through stopcock valve 19, when in an open position, and out exit port 21. Stopcock valve 19 may be in the off position, or closed, when an effective amount of fluid has been dispensed and no more fluid flow is desired, for example, when the fluid level within the organ is to be maintained for a period of time.

When the fluid pressure is greater than a predetermined level, such as the tolerance limit of the pressure relief valve, for example, if the fluid pressure is greater than 200 mm Hg, pressure relief valve 14 opens and fluid flows from pressure relief valve 14 to tubing 15. Stopcock valve 19 is closed to prevent retrograde flow of fluid and to maintain the dispensed fluid. When the fluid pressure drops below the predetermined level, pressure relief valve 14 closes, stopcock valve 19 is opened and fluid may again be moved from first container 13. As shown in FIG. 1, fluid entering tubing 15 may enter second container 16. Second container may or may not be a closed container, and may or may not have indicating element 18 in place. When the liquid enters second container 16, indicating element 18 moves in a proximal direction away from the entrance of second container 16. Alternatively, not shown in FIG. 1, pressure relief valve 14 may be connected to tubing 15 which provides an exit for the pressure valve released fluid from the device. A container not within fluid pressure control device 10 may be accessed by tubing 15 to provide the released fluid to the container.

In use of fluid pressure control device 10, a catheter, such as a uterine access catheter, may be attached at exit port 21. Thus, fluid would flow from first container 13, through pressure relief valve 14, through stopcock valve 19, out exit port 21 and into and through the uterine access catheter to provide fluid to the uterus and fallopian tubes.

Device 10 may be filled with fluid by optionally attaching a needle to the attachment element of exit port, and placing it in a container of fluid, alternatively exit port 21 may be immersed in the fluid. Moving plunger knob 12 in a proximal direction to draw the plunger body through container 13 creates space in container 13 and lower pressure so that fluid moves into exit port 21, through stopcock 19, through relief valve 14 and into container 13. In general, the devices disclosed herein may be filled in this manner.

The fluid pressure control device of the present invention may be combined with other devices to provide fluid pressure control of fluids dispensed. For example, fluid pressure control device elements of the present invention may be combined with devices that generate a contrast medium composition. Fluid pressure control device elements of the present invention may be combined with devices that provide fluids directly to at least a fallopian tube and/or uterus.

Figure 2:
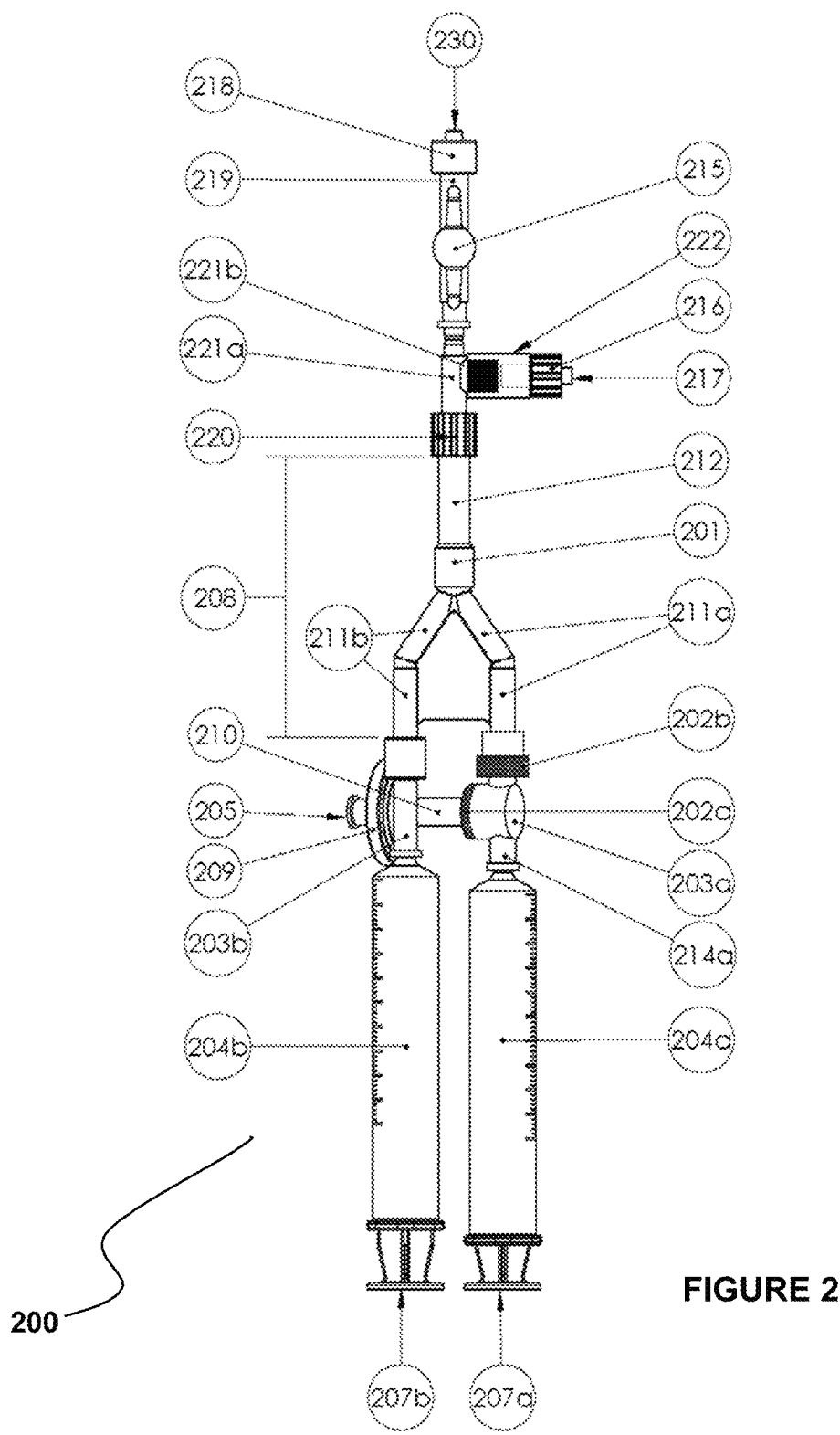
FIG. 2 shows an exemplary combined fluid pressure control and contrast medium generating device.

The present invention comprises methods, devices and systems comprising combination devices comprising elements for making a contrast medium composition as disclosed in U.S. patent application Ser. Nos. 12/245,265 and 13/219,667, each of which is herein incorporated in its entirety, in combination with fluid pressure control elements disclosed herein. As used herein, contrast agent and contrast medium mean a composition that is visible by ultrasound methods, referred to as sonography, and also comprises fluorographic media, visible by X-ray technologies, and the terms may be used interchangeably. Methods of the present invention comprise use of a contrast agent that is useful for observing organs or body structures, for example, the uterus and fallopian tubes. An example of a combination device, combined fluid pressure control and contrast medium generating device, is shown in FIG. 2.

A combined fluid pressure control and contrast medium generating device comprises a container assembly and optionally, a catheter assembly fluidly coupled to the container assembly, and fluid pressure control elements. A container assembly may comprise at least one container for a fluid. A fluid may be a liquid or a gas. A container assembly may comprise a first container for a liquid, such as saline, and a second container for a gas, such as air, and elements for creating an alternating pattern of gas and fluid. A container assembly may comprise connection elements, such as tubing or fluid conduits, for providing the contained fluid from a container to a contrast pattern generating chamber and to the catheter assembly, or from the exterior of the container assembly to a contrast pattern generating chamber and to a container. The connection elements may be used for providing fluids from the exterior of the device to the containers. A container may comprise one or more outlets through which the fluid, such as gas or liquid or combination/alternating delivery of saline and air, exits the container, or the outlet may be used to provide a fluid, either liquid or gas or combination into the container. A container assembly may comprise a component for providing force upon the fluid contained within the container to move fluid into, or out of, the container. For example, a container may be a syringe body or barrel, and the component for providing force upon the fluid is a syringe plunger. The container assembly may comprise a component for activating the component for providing force. For example, the container may be a syringe body or barrel, the component for providing force upon the contained fluid is a syringe plunger, and the component for activating the plunger may be a pump, or the hand of an operator. An aspect of the invention comprises an embodiment where the contrast medium device comprises two containers, such as two syringe bodies, and the syringe plungers are moved in concert because the two plunger ends are held together by a component, such as an actuator, such that the syringe plungers move through the interior of the barrel of the syringes at the same rate, speed and distance through the interior. The syringe plungers move at the same rate, speed and distance because the proximal ends of each plunger are linked together, such as by an element, an actuator.

The container assembly may further comprise fluid connections, which are fluid connecting elements between elements that are in fluid connection with one another, such as the one or more containers and a contrast pattern generating chamber. Such fluid connections include, but are not limited to, conduits, tubing or needles. The container assembly may comprise a contrast pattern generating chamber wherein a gas phase and a liquid phase are admixed and the composition exiting the contrast pattern generating chamber, the contrast medium composition, is characterized by alternating phases of gas and liquid which form the pattern of the contrast medium composition. The container assembly may comprise fluid connections which provide the contrast medium composition to a catheter assembly or directly to a structure to be visualized.

In an embodiment, a contrast medium device may comprise a container that may function as a contrast pattern generating chamber, wherein the contrast medium is made within the container, no contrast pattern generating chamber is present, and the contrast medium composition, for example comprising gas and liquid phases, is provided to the exterior of the contrast medium device.

An example of a combined fluid pressure control device and contrast medium generating device 200 is shown in FIG. 2. FIG. 2 is an illustration of a combination of components of a contrast medium generating device and a fluid pressure control device. In the device 200 of FIG. 2, the first container 13 (as shown and numbered in FIG. 1), is not present and is replaced, starting at connector 207 by at least components number 201-205, 207-208, 210-212, 214. Plunger ends 207a and 207b, are attached to syringe plungers (not shown) maintained within the syringe bodies 204a and 204b. Not shown is an element connecting the two plunger ends so that plunger ends 207a and 207b may be actuated simultaneously. Though the plungers are described as moving individually herein for ease of understanding, it is contemplated by the present invention that the plungers may move simultaneously to deliver fluid and/or to load or refill fluid. Also not shown is the entire length of each plunger, wherein each plunger end may be connected to a piston and a fluid seal displaced within the syringe body.

Syringe body (Container) 204b is hollow and can contain a liquid, such as saline, and is in fluid connection with a conduit for fluid, connection 203b. Connection 203b connects to contrast medium generating chamber 208, which comprises a conduit in fluid connection respectively with each container (connections 211a and 211b) and a mixing chamber 201, and static mixer 212. Syringe body (Container) 204a is hollow and can contain a gas, and is in line and in gas connection with a check valve 202a that is line with connection 210 in the air path from the air port opening 205. Connection 210 is in line and in fluid connection with an air filter 209 which is in line and in fluid connection with an air port opening 205. For filling container 204a, air can be drawn in through air port opening 205, into and through filter 209, through connection 210, through check valve 202a, through connection 203a, through container exit port 214a and into container 204a. For providing air to contrast medium generating chamber 208, air is moved from container 204a through container exit port 214a and into connection 203a by applying pressure to plunger end 207a, which moves the plunger piston and fluid seal through the interior body of container 204a, from a proximal to a distal location, where proximal is in the direction away from exit port 230 and distal is in the direction of exit port 230. Check valve 202b is in fluid (gas) communication with contrast generating chamber 208 so that gas from container 204a is moved from container 204a, through container exit port 214a, through connection 203a, through check valve 202b, to the proximal end of contrast medium generating chamber 208 at connection 211a in contrast generating chamber 208 and to the mixing chamber 201, which may comprise a static mixer 212.

In providing saline or any other fluid to contrast medium generating chamber 208, saline (or other fluid) is moved from container 204b into connection 203b by applying pressure to plunger end 207b, which moves the plunger piston and fluid seal through the interior body of container 204b. From connection 203b, saline enters the proximal end of contrast medium generating chamber 208, comprising connection 211b, which is in line and in fluid connection with mixing chamber 201. The distal end of contrast medium generating chamber 208 is in fluid connection with static mixer 212, and exit port 230.

In filling the device of FIG. 2 with a liquid, such as saline, exit port 230 or an attachment to exit port 230, such as a needle, is immersed in the fluid, such as saline, found in a container such as a bowl or other container of fluid. The piston and fluid seal end of plunger 207b are located in a more distal position within container 204b, and a force is applied to move the plunger end, and the piston and fluid seal, away from exit port 230 and towards the proximal end of container 204b. As the fluid seal moves through the container in a proximal direction, saline is drawn into and through exit port 230, through the contrast medium generating chamber 208 and connections 211a and 211b, where saline is prevented from flowing any further than 211a connection by check valve 202b (a one way valve), and saline continues to flow through connection 203b, and into container 204b.

For filling container 204a, air can be drawn in through air port opening 205, into and through filter 209, through connection 210, through check valve 202a, through connection 203a, and into container 204a. For providing air to contrast medium generating chamber 208, air is moved from container 204a into connection 203a by applying pressure to plunger end 207a, which moves the plunger piston and fluid seal through the interior body of container 204a. Check valve 202b is in fluid (gas) communication with contrast generating chamber 208 so that gas from container 204a is moved from container 204a, through container exit port 214a, through connection 203a, through check valve 202b, to the proximal end of contrast medium generating chamber 208 at connection 211a in contrast generating chamber 208 and to the mixing chamber 201, which may comprise a static mixer 212.

The distal end of connector 220 is in line and in fluid connection with a channel 221a of the pressure relief portion, comprising at least elements 221a, 221b, 222, 215, 216, 217 and 219. Channel 221a of the pressure relief portion is in fluid connection with connection 219, comprising a stopcock valve 215, which can be in an open or closed position by use of the stopcock handle of stopcock valve 215, and in line and in fluid connection with connector 218 and exit port 230. Pressure relief valve 221b is in a closed position and is opened when the fluid pressure at the valve exceeds the allowed pressure. When the allowed pressure is exceeded, relief valve 221b opens, and fluid flows from channel 221a (or from connection 219 to channel 221a) through relieve valve 221b and into and through connector 216, which is connected to the relief valve 221b by way of tubing connection 222. Connector 216 is an attachment element for attaching a container, bag or collection device (not shown) for the fluid flowing through exit port 217. If relief valve 221b opens, stopcock valve 215 may be turned to closed by moving the stopcock valve 215 handle so that fluid ceases to flow to relief valve 221b. Attachment element 218 may be attached to a catheter, not shown. Fluid exits exit port 230 into a catheter and is provided to an organ, cavity or a conduit.

The present invention comprises combination devices for delivery of a fluid, such as a contrast medium or treatment medium, to a structure with fluid pressure control. It is contemplated by an embodiment of the present invention that the fluid is provided by the catheter assembly directly into the uterus, fallopian tubes, or directly to a structure to be treated or visualized. The amount of fluid used may be any amount, for example, it may be an amount that is sufficient to provide an accurate visualization or effective treatment of the structure. The contrast fluid may substantially fill the structure visualized, or may only be present in particular locations within the structure. A treatment fluid may substantially fill the structure, or may only be present in particular locations within the structure.

Figure 3:
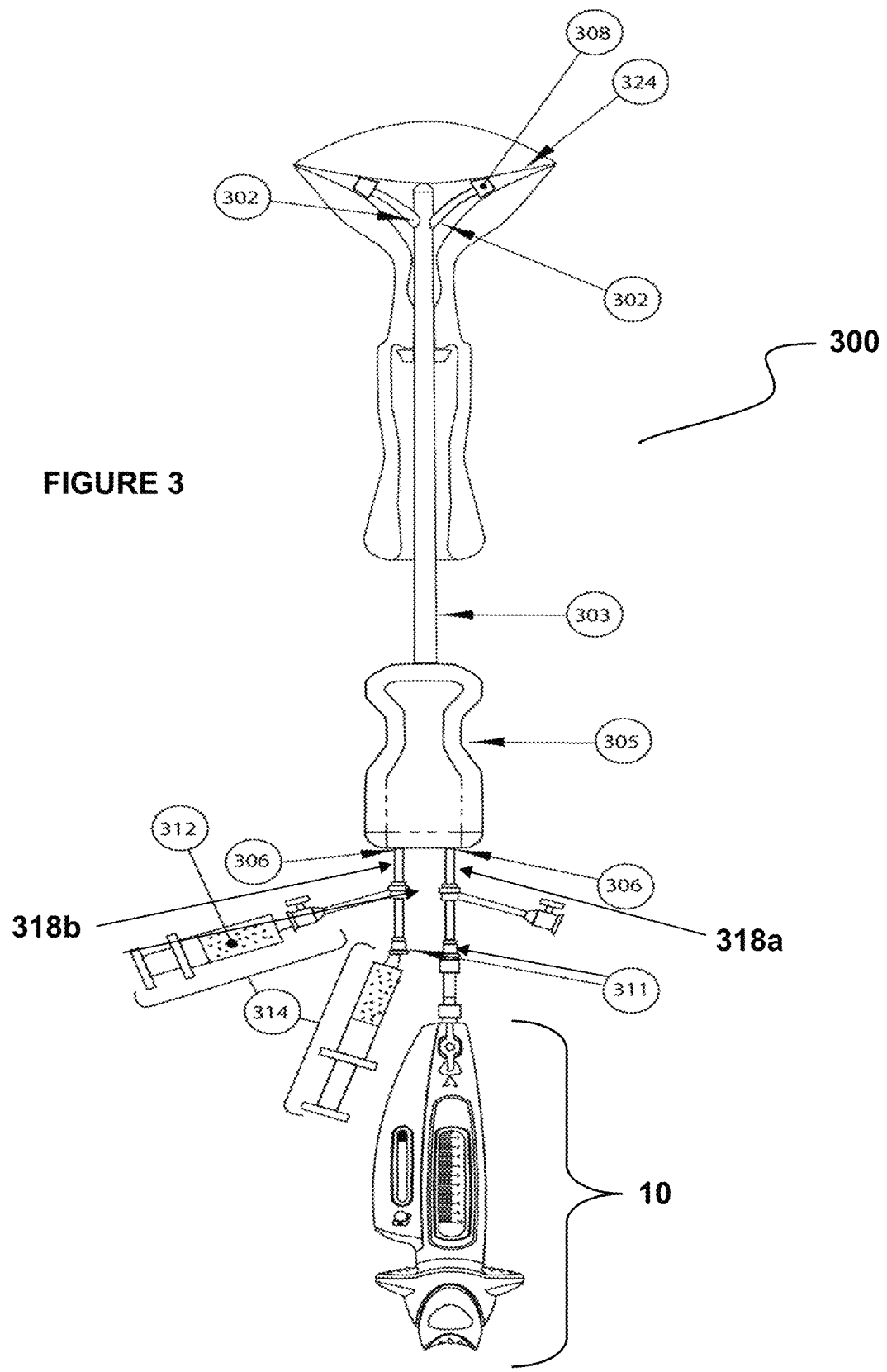
FIG. 3 shows an exemplary device system comprising a fluid pressure control device and a catheter delivery device.

When the structure to be visualized or treated is a fallopian tube, combination device comprising a catheter delivery device that provides a catheter to the uterus and/or fallopian tube may be used. The attachment end of a catheter (on the proximal end of the catheter, as shown) may be connected to the exit port of a fluid pressure control device described herein. Devices for providing a catheter to a body structure, such as a fallopian tube, and are useful in methods of accessing a fallopian tube are taught in U.S. Pat. Nos. 8,048,086; 8,048,101; 8,052,669 and U.S. patent application Ser. No. 12/504,912, each of which is herein incorporated in its entirety, and referred to herein as a catheter delivery device. In general, disclosed are catheter delivery devices comprising an introducer shaft that is used to enter and traverse the uterus until the tip of the shaft approaches or touches the fundus of a uterus. Once the tip of the introducer shaft is at the fundus of the uterus, the device may be stabilized. One or more catheters, 318a and/or 318b, such as two as in FIG. 3, are fed through the introducer shaft and exit out into the uterine cavity. The placement of the introducer shaft allows for the three dimensional alignment of the catheter(s) with the cornua of the uterus. The catheter(s) is advanced until the delivery end(s) of the catheter(s) are in place in the cornua. An end structure, such as a balloon, cup, or nozzle is inflated or engaged, to stabilize the catheter(s) in the tubal ostia, and the end structure may prevent or minimize back-flow of materials exiting the catheter delivery end. Once the end structure is engaged, the catheter(s) is ready for delivery of materials or other activities. A fluid may be delivered with a fluid pressure control device of the present invention attached in place of one or more cartridges attached to one or more catheters provided by the introducer shaft device.

Figure 4:
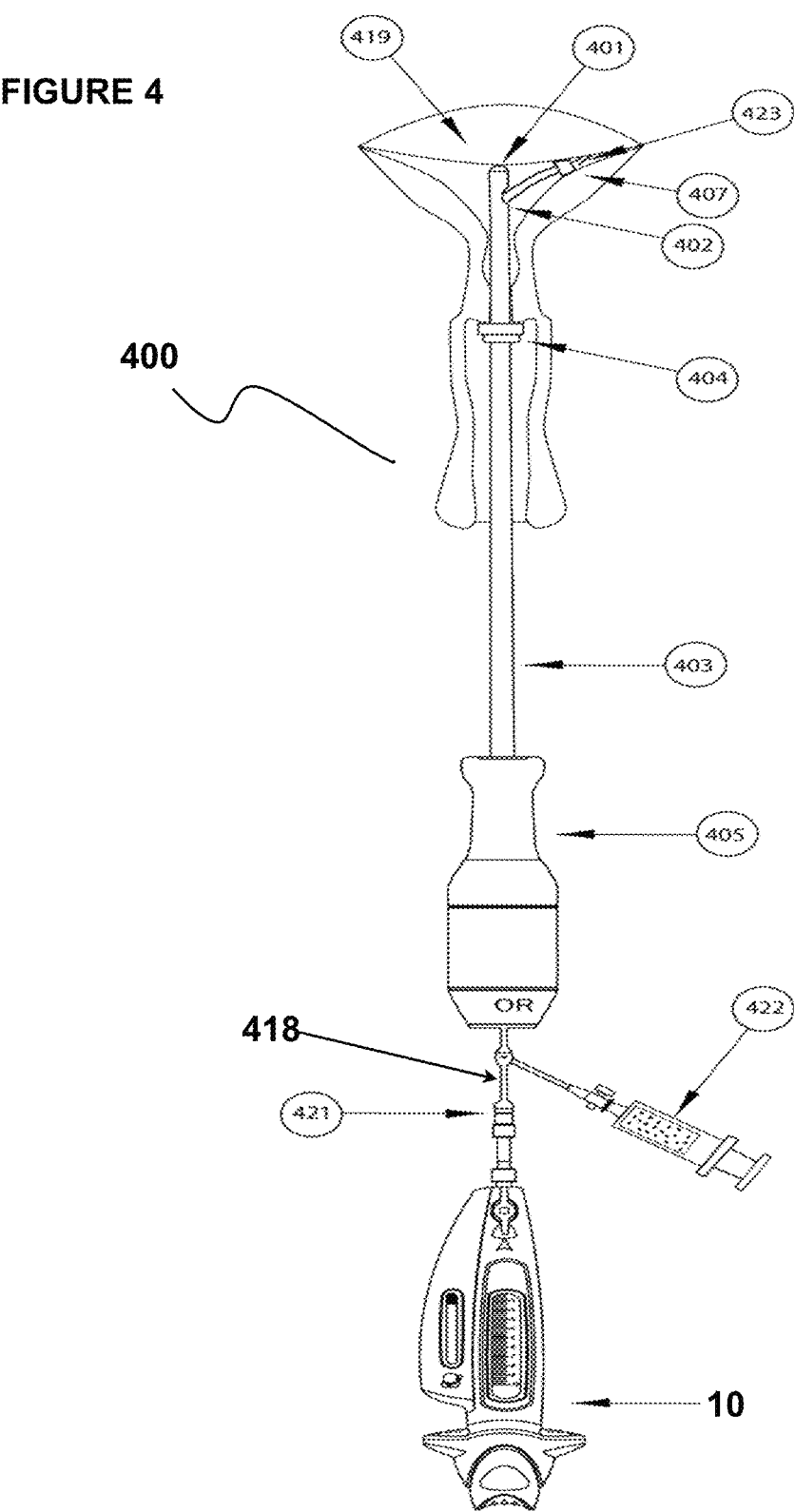
FIG. 4 shows an exemplary device system comprising a fluid pressure control device and a catheter delivery device.

For example, see FIG. 3, wherein a catheter delivery device as taught in U.S. Pat. Nos. 8,048,086; 8,048,101; 8,052,669 and U.S. patent application Ser. No. 12/504,912 is used to provide a fluid to the uterus and/or fallopian tubes. Though as shown in FIGS. 3 and 4, fluid pressure control device 10 is illustrated, it is to be understood that a fluid pressure control disclosed herein could be used, and the invention is not limited by the illustrations. A cartridge or syringe unit labeled 314 is replaced with a fluid pressure control device, for example, the device as in FIG. 1. FIG. 3 depicts a catheter delivery system for the introduction of fluid. With the introducer shaft 303 in position with the closed tip at the fundus of the uterus, the operator moves a double-lumen catheter(s) 318a/318b through catheter insertion hole 306 through the introducer shaft lumens until each catheter exits the introducer shaft lumen exit port 302, and the delivery end (the distal end) of the catheter is located within the uterine cornua 324 as determined by the operator's tactile feel, imaging such as ultrasound, or a combination of feel and imaging.

When the delivery end of catheter 318 is positioned within the uterine cornua 324, the catheter position may be maintained by a locking mechanism which may be attached to the housing 305 at or near the catheter insertion hole 306, at another location within housing 305, or by a mechanism that is separate from housing 305 and which serves to grab, clamp, hold or otherwise stabilize the catheter such that it does not move and such that the delivery end remains in the target location. In another aspect of the invention, inflation of a balloon or other end structure of catheter 318a/b is sufficient to maintain position of the catheter, and no additional locking mechanism may be required.

A cartridge 312 containing balloon distension medium may be attached to a fitting and delivered to effect inflation of an end structure 308. Distension medium may comprise any flowable or liquid material suitable for inflation of the end structure 308, such material being chemically compatible with the material of the end structure 308 and may be biologically compatible in the event distension medium is introduced into the uterine cavity or fallopian tubes. Exemplary distension media include, but are not limited to, air and sterile isotonic saline solution. The cartridge 312 may be disconnected and the procedure repeated to inflate the balloon on the contralateral side. The balloons may be distended simultaneously using two cartridges. A fluid pressure relief device of the present invention, for example as described in FIG. 1, may be attached to catheter 318a/b at fitting 311, and replace the syringe cartridge 314. As described for FIG. 1, fluid is provided from a fluid pressure control device, when container 13 contains fluid, and the plunger body, fluid seal element and plunger knob are at a proximal location, such as placing the fluid seal element near the proximal end of container 13, plunger knob 12 is moved from a proximal location to a more distal location. Slidable movement of the plunger body with the fluid seal element moves liquid from first container 13 through at least pressure relief valve 14, through stopcock valve 19, when in an open position, and out exit port 21. The fluid from container 13 moves into and through the catheter, and exits through the delivery end of the catheter 307 toward the target location for example, the ostia and tubal region of a fallopian tube.

An alternative catheter delivery device is shown in FIG. 4. The present invention comprises methods and devices, for example, as shown in FIG. 4, wherein a catheter delivery device in combination with a fluid pressure control device is used to deliver a fluid to the uterus and/or at least one fallopian tube. When the introducer shaft of the catheter delivery device is in position, a catheter, such as a double-lumen balloon catheter, is advanced out of an introducer lumen until it exits the single exit port and enters the uterine cornua, the placement of the delivery end of the catheter may be determined by sensation of the operator (by feel) or by ultrasound or by both methods.

In FIG. 4, an operator holds the introducer housing 405 and inserts the shaft of the introducer 403 through the cervix until the atraumatic tip 401 contacts the uterine fundus 419 as determined by tactile feel, visualization such as ultrasound, or a combination of both tactile feel and visualization. When the atraumatic tip 401 is appropriately placed, such as against the uterine fundus, the introducer shaft lumen exit port 402 is located such that the opening is directed toward the uterine cornua 423. Optionally, following contact of the atraumatic tip 401 with the uterine fundus 419, the delivery device stabilizer 404 is moved into position. In one embodiment, the delivery device stabilizer 404 may comprise components or structures that function to ensure that the operator maintains a fixed position of the introducer shaft, for example for preventing uterine perforation, as well as maintaining the position of the shaft lumen exit port 402 during the procedure. In another embodiment, the delivery device stabilizer 404 may comprise components or structures to provide a depth stop mechanism or uterine length marker to the delivery device. In still another embodiment, the delivery device stabilizer 404 comprises components or structures to provide a depth stop mechanism or uterine length marker and stabilization to the delivery device. Such stabilizers are taught in the referenced patents and applications.

With the introducer in position, the operator moves a catheter 418, such as a double-lumen catheter which may be pre-loaded into the introducer shaft lumen, allowing catheter 418 to exit the introducer shaft lumen at exit port 402, and the delivery end 407 of catheter 418 is located at or within the uterine cornua 423 as determined by the operator's tactile feel, imaging such as ultrasound, or a combination of feel and imaging. Once the delivery end 407 of the catheter is positioned within the uterine cornua 423, the catheter position may be maintained by a locking mechanism which may be attached to the housing or at another location within the housing, or by a mechanism that is separate from the housing, which serves to grab, clamp, hold or otherwise stabilize the catheter such that it does not move and such that the delivery end remains in the target location. In another aspect of the invention, an end structure 407 of the catheter may be used, for example by inflation of a balloon to maintain position of the catheter, and no additional locking mechanism may be required, or a balloon or end structure may be used with one of the catheter stabilizing components. For example, if a balloon catheter is used, a cartridge containing balloon distension medium 422 which has been previously prepared or mixed if such mixing is necessary, is then fitted to a fitting and the distension medium delivered to effect inflation of the balloon. Distension medium may comprise any flowable or liquid material suitable for inflation of the balloon, such material being chemically compatible with the material of the balloon and may be biologically compatible in the event distension medium is introduced into the uterine cavity or fallopian tubes. Exemplary distension media include, but are not limited to, air and sterile isotonic saline solution. Following inflation of the balloon, cartridge 422 may be disconnected from the fitting or is automatically held inflated by a mechanism in the introducer housing element.

A fluid pressure control device 430, such as one described in FIG. 1, is attached at exit port 21 to catheter fitting 421. As described for FIG. 1, fluid is provided from a fluid pressure control device, when container 13 contains fluid, and the plunger body, fluid seal element and plunger knob are at a proximal location, such as placing the fluid seal element near the proximal end of container 13, plunger knob 12 is moved from a proximal location to a more distal location. Slidable movement of the plunger body with the fluid seal element moves liquid from first container 13 through at least pressure relief valve 14, through stopcock valve 19, when in an open position, and out exit port 21. The fluid from container 13 moves into and through the catheter, and exits through the delivery end 407 of the catheter 418 toward the target location 423 for example, the ostia and tubal region of a fallopian tube.

A method of the present invention comprises providing fluid at or below a predetermined pressure through one or more catheters to a target location, wherein a fluid pressure control device as described herein is used in place of a fluid providing container or device, for example, a syringe device. Exemplary replacement of fluid providing containers by fluid pressure control devices are shown in FIGS. 2, 3 and 4, but the present invention is not limited to only the disclosed embodiments, but contemplates devices and systems comprising fluid pressure control devices in place of fluid containers, and use of devices and systems comprising fluid pressure control devices in place of fluid containers, for methods, systems and devices where a controlled fluid pressure would be desired.

Contrast media may comprise pharmacologically acceptable x-ray opaque substances or may comprise sonographically detectable compositions. Contrast media may comprise oil soluble, water soluble, low osmolarity water soluble, and high osmolarity water soluble materials. In an aspect, contrast media is selected from iohexol, iodixanol, ioversol, diatrizoate, metrizoate, ioxaglate, iopamidol, ioxilan, Lipiodol, diatrizoate meglumine, and ethiodized poppy-seed oil. In an aspect, contrast media is an iodinated contrast media and is selected from oil soluble; water soluble; iso-osmolar and low osmolar; and, non-ionic, and water-soluble. In an aspect, the contrast media is an iodinated, low osmolality non-ionic material. In an aspect, the contrast media comprises iohexol, ioxaglate, diatrizoate meglumine, and ethiodized poppy-seed oil.

Compositions of the present invention comprise a visualizable composition which may be referred to herein as a contrast medium. A contrast medium of the present invention may comprise a gas phase within a liquid carrier. The gas phase may be a bubble or may be a liquid-free, gas-filled area adjacent to a liquid phase area, and the alternating gas-filled area and liquid area may repeat multiple times. The sizes of the gas-filled areas or the liquid filled areas may be uniform in size or not. In an aspect, contrast medium may be provided in reduced volumes, compared to amounts currently used which may be 20 mL or more, by providing the contrast medium substantially in or very near the structure to be visualized (i.e. fallopian tube). The present invention controls the amount of gas and liquid used in combination to form the mixed gas/liquid composition, which enters the structure. The pattern of the contrast medium composition can range from predominantly a gas (air or other gas) phase to predominantly a liquid (saline or other liquid) phase and can be provided in a regular pattern or in an irregular pattern. The ratios of the gas to liquid may be determined by the size of the respective syringe. The larger the air syringe the greater the air segment in the pattern of the composition. The use of a porous structure may create a more random or irregular pattern. The amount of contrast medium delivered may be controlled by the amount of syringe plunger displacement.

A composition of the present invention may comprise a liquid and a gas, and optionally, surfactants, emulsifiers, or other stabilizing agents. The liquid, which may be seen as a carrier of the gas phase, may be any liquid that is substantially free of solids and flows at normal or body temperatures. For example, the liquid may be water or physiologically acceptable aqueous solutions including, but not limited to, physiological electrolyte solutions, physiological saline solutions, Ringer's solution or aqueous solutions of sodium chloride, calcium chloride, sodium bicarbonate, sodium citrate, sodium acetate, or sodium tartrate, glucose solutions, or solutions or mono- or polyhydric alcohol, e.g., ethanol, n-butanol, ethylene glycol, polyvinylpyrrolidone, or mixtures or combinations of these. Further, the liquid carrier may comprise physiologically acceptable non-aqueous solutions, including, but not limited to, anhydrous or substantially anhydrous carrier liquids, alcohols, glycols, polyglycols, synthetic perfluoranated hydrocarbons, or in mixtures or combination with other non-aqueous or aqueous liquids.

The contrast media or visualizable compositions of the present invention may comprise surfactants or compounds that stabilize the gas-liquid interface. Surfactant composition may be useful when the contrast medium is provided to a structure that is larger than the catheter size used to transmit the contrast medium. Surfactants include tensides, such as lecithins; esters and ethers of fatty acids and fatty alcohols with polyoxyethylene and polyoxyethylated polyols like sorbitol, glycols and glycerol, cholesterol; and polyoxy-ethylene-polyoxypropylene polymers, viscosity raising and stabilizing compounds, mono- and polysaccharides (glucose, lactose, sucrose, dextran, sorbitol); polyols, e.g., glycerol, polyglycols; and polypeptides like proteins, gelatin, oxypolygelatin, plasma protein, amphipathic compounds capable of forming stable films in the presence of water and gases, such as the lecithins (phosphatidyl-choline) and other phospholipids, inter alia phosphatidic acid (PA), phosphatidylinositol, phosphatidylethanolamine (PE), phosphatidylserine (PS), phosphatidylglycerol (PG), cardiolipin (CL), sphingomyelins, the plasmogens, the cerebrosides, natural lecithins, such as egg lecithin or soya bean lecithin, or synthetic lecithins such as saturated synthetic lecithins, for example, dimyristoylphosphatidylcholine, dipalmitoylphosphatidylcholine or distearoylphosphatidylcholine or unsaturated synthetic lecithins, such as dioleylphosphatidylcholine or dilinoleylphosphatidylcholine, free fatty acids, esters of fatty acids with polyoxyalkylene compounds like polyoxypropylene glycol and polyoxyalkylene glycol; ethers of fatty alcohols with polyoxyalkylene glycols; esters of fatty acids with polyoxyalklated sorbitan; soaps; glycerol-polyalkylene stearate; glycerol-polyoxyethylene ricinoleate; homo- and copolymers of polyalkylene glycols; polyethoxylated soya-oil and castor oil as well as hydrogenated derivatives; ethers and esters of sucrose or other carbohydrates with fatty acids, fatty alcohols, these being optionally polyoxyalkylated; mono- di and triglycerides of saturated or unsaturated fatty acids; glycerides of soya-oil and sucrose, block copolymers of polyoxypropylene and polyoxyethylene (poloxamers), polyoxyethylenesorbitans, sorbitol, glycerol-polyalkylene stearate, glycerolpolyoxyethylene ricinoleate, homo- and copolymers of polyalkylene glycols, soybean-oil as well as hydrogenated derivatives, ethers and esters of sucrose or other carbohydrates with fatty acids, fatty alcohols, glycerides of soya-oil, dextran, sucrose and carbohydrates. Surfactants may be film forming and non-film forming and may include polymerizable amphiphilic compounds of the type of linoleyl-lecithins or polyethylene dodecanoate, phosphatidic acid, phosphatidylcholine, phosphatidylethanolamine, phosphatidylserine, phosphatidylglycerol, phosphatidylinositol, cardiolipin, sphingomyelin and biocompatible and amphipathic compound capable of forming stable films in the presence of an aqueous phase and a gas, phospholipids including phosphatidylcholine (PC) with both saturated and unsaturated lipids; including phosphatidylcholine such as dioleylphosphatidylcholine; dimyristoylphosphatidylcholine (DMPC), dipentadecanoylphosphatidylcholine-, dilauroylphosphatidylcholine (DLPC); dipalmitoylphosphatidylcholine (DPPC); disteraoylphosphatidylcholine (DSPC); and diarachidonylphosphatid-ylcholine (DAPC); phosphatidylethanolamines (PE) such as dioleylphosphatidylethanolamine, dipaimitoylphosphatidylethanolamine (DPPE) and distearoylphosphatidylethanolamine (DSPE); phosphatidylserine (PS) such as dipalmitoyl phosphatidylserine (DPPS), disteraoylphosphatidylserine (DSPS); phosphatidylglycerols (PG), such as dipalmitoylphosphatidylglycerol (DPPG), distearoylphosphatidylglycerol (DSPG); and phosphatidylinositol.

Contrast medium compositions may comprise gases, and any physiologically acceptable gas may be present in the compositions of the present invention. The term "gas" as used herein includes any substances (including mixtures) substantially in gaseous form at the normal human body (37° C.). Close to 200 different gases have been identified as potentially useful for making ultrasound contrast agents, and include oxygen, air, nitrogen, carbon dioxide or mixtures thereof, helium, argon, xenon, krypton, $CHClF_2$ or nitrous oxide, sulfur hexafluoride, tetrafluoromethane, chlorotrifluoromethane, dichlorodifluoromethane, bromotrifluoromethane, bromochlorodifluoromethane, dibromodifluoromethane dichlorotetrafluoroethane, chloropentafluoroethane, hexafluoroethane, hexafluoropropylene, octafluoropropane, hexafluoro-butadiene, octafluoro-2-butene, octafluorocyclobutane, decafluorobutane, perfluorocyclopentane, dodecafluoropentane, fluorinated gases including materials which contain at least one fluorine atom such as SF6, freons (organic compounds containing one or more carbon atoms and fluorine, i.e. $CF_4$, $C_2F_6$, $C_3F_8$, $C_4F_8$, $C_4F_{10}$, $CBrF_3$, $CC_{12}F_2$, $C_2ClF_5$ and $CBrClF_2$ and perfluorocarbons. The term perfluorocarbon refers to compounds containing only carbon and fluorine atoms and includes saturated, unsaturated, and cyclic perfluorocarbons such as perfluoroalkanes such as perfluoromethane, perfluoroethane, perfluoropropanes, perfluorobutanes (e.g. perfluoro-n-butane, optionally in admixture with other isomers such as perfluoro-isobutane), perfluoropentanes, perfluorohexanes and perfluoroheptanes; perfluoroalkenes such as perfluoropropene, perfluorobutenes (e.g. perfluorobut-2ene) and perfluorobutadiene; perfluoroalkynes such as perfluorobut-2-yne; and perfluorocycloalkanes such as perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane.). The saturated perfluorocarbons, which are usually preferred, have the formula CnFn+2, where n is from 1 to 12, preferably from 2 to 10, most preferably from 3 to 8 and even more preferably from 3 to 6. Suitable perfluorocarbons include, for example, $CF_4$, $C_2F_6$, $C_3F_8$, $C_4F_8$, $C_4F_{10}$, $C_5F_{12}$, $C_6F_{12}$, $C_7F_{14}$, $C_8F_{18}$, and $C_9F_{20}$.

Treatment compositions of the present invention may comprise diagnostic or therapeutic compositions that may be provided to humans or animals. Treatment compositions may comprise therapeutic agents. For example, treatment compositions may be provided to an altered organ or unaltered organ, as described herein. For example, treatment compositions may comprise, but are not limited to, methotrexate, chemotherapeutic compositions, radionuclide comprising compositions, hormones, fertility enhancing compounds, fertility interfering compounds, motility enhancing compounds, motility interfering compounds, compounds affecting the cilia/deciliation cycle, cilia growth enhancing or interfering compounds, ovarian follicle treatment compounds, antibacterial, antimicrobial, antifungal, antiviral, antimycoplasmal, or antiparisital compounds, compounds that reduce inflammation or scar tissue formation, composition comprising one or more antibiotics, antimycoplasma agents, or antiviral compounds; compositions comprising mucoproteins, electrolytes or enzymes to enhance or inhibit fertility, progesterone, estrogen, adrenergic active compounds, noradrenergic active compounds, nonsteroidal anti-inflammatory drug, prostaglandins, other compounds that may treat or prevent conditions related to the fallopian tube, uterus, ovaries, or other organs or coverings reached by a composition flowing from the cornua or ostia of a fallopian tube or combinations thereof. Treatment compositions may comprise hormones for fertility, fertility enhancing compounds, gametes, sperm, ova, combinations of sperm and ova, one or more zygotes, or one or more embryos, or combinations thereof. Compositions may comprise the intermingling of a gas with the treatment compositions, and delivery of the compositions may be monitored by techniques such as ultrasound. A composition comprising therapeutic agents combined with the interfaces created by combining a gas with the therapeutic composition using a device of the present invention may provide both treatment and diagnosis of the condition of a structure in one step of delivering the composition. Alternatively, a combined therapeutic agent composition with interfaces from gas/liquid phases may be employed to limit or locate the medicament in the targeted structure with the support of sonographic imaging allowing for diagnosis and treatment to occur simultaneously or in sequence.

The invention sets forth particular devices that can be useful for the methods described. However, one skilled in the art can utilize other devices and methods for relieving pressure, regulating flow and thereby stabilizing pressure, and containing fluid once pressure is achieved.

An aspect of the invention comprises a method for performing hysterosalpingography on a patient having an altered organ, comprising, providing a catheter assembly including a catheter, optionally having a balloon, for example in a location near its distal end, introducing the catheter assembly through the patient's vagina so that the balloon is positioned past the cervix and in the uterus; inflating the balloon to seal against the cervix; introducing a liquid, such as contrast media or a treatment fluid, through the inner catheter into the uterus. The method may comprise imaging an altered organ, or associated altered or unaltered organs, such the uterus and one or more of the fallopian tubes which may have undergone a sterilization procedure such as occluding, blocking or ligation or severance of one or more fallopian tubes, wherein a visualizable fluid is provided. The method may comprise treating an altered organ, or associated altered or unaltered organs, such the uterus (unaltered) and one or more of the fallopian tubes (altered) which may have undergone a sterilization procedure such as occluding, blocking or ligation or severance of one or more fallopian tubes, wherein a treatment fluid is provided. The fluid is provided to the uterus and/or fallopian tube(s) at a pressure that does not exceed a predetermined level, for example, 200 mm Hg, by a fluid pressure control system and device comprising a check valve, a relief valve and/or a constant force spring.

In an aspect, the present invention comprises a constant force spring fluid pressure control device. In an aspect, the constant force spring fluid pressure control device comprises components shown in FIG. 5. In an aspect, the constant force spring fluid pressure control device comprises delivery of a fluid composition disclosed herein wherein spring 505 is charged or cocked by extending spring ends 501a, 501b which are attached to the plunger head 502, in a proximal direction away from the exit port 503. Plunger head 502 is held in place by trigger 504. Fluid is contained in container 506, shown here as a syringe. Trigger 504 is moved to release plunger head 502 and attached spring ends 501, allowing for the fluid to be moved at a constant flow rate and to be delivered at a flow to not exceed the maximum desired or predetermined pressure, for example, of about 150-200 mm Hg. Movement through container 506 by plunger 507 is represented by the circles shown within container 506. In an aspect, a method using the constant force spring fluid pressure control device may comprise delivery of a fluid using a piston pump, a roller pump, or a peristaltic pump to control plunger head 502 and may be powered electrically or mechanically. The device may also operate using a constant force to propel the fluid through a narrow tube which determines or regulates the flow rate. The constant force spring fluid pressure control device may be filled by placing the exit port, or a needle attached to the exit port, in fluid and moving the plunger body in a proximal direction to draw fluid into container 506. The plunger head 502 engages trigger 504 and is held in place, ready to be released and deliver fluid.

In an aspect, the present invention comprises a dual syringe fluid pressure control device such that the second barrel serves as a reservoir/drain and point of pressure control. Other containers may be used in place of the syringes. In an aspect, the dual syringe fluid pressure control device comprises the device shown in FIG. 6. In an aspect, the dual syringe fluid pressure control device comprises a plunger driven spring of appropriate tension to exert the necessary fluid pressure, where the operator charges the syringe with fluid and then advances the plunger to deliver fluid for example into a catheter and on into an organ, cavity or a conduit, a body structure, until the spring pressure is surpassed by the fluid pressure, at which point the spring undergoes compression and maintains the desired pressure until it reseats itself due to leakage or other flow. Upon re-seating the operator may continue with further delivery until again the predetermined pressure is reached.

Figure 6:
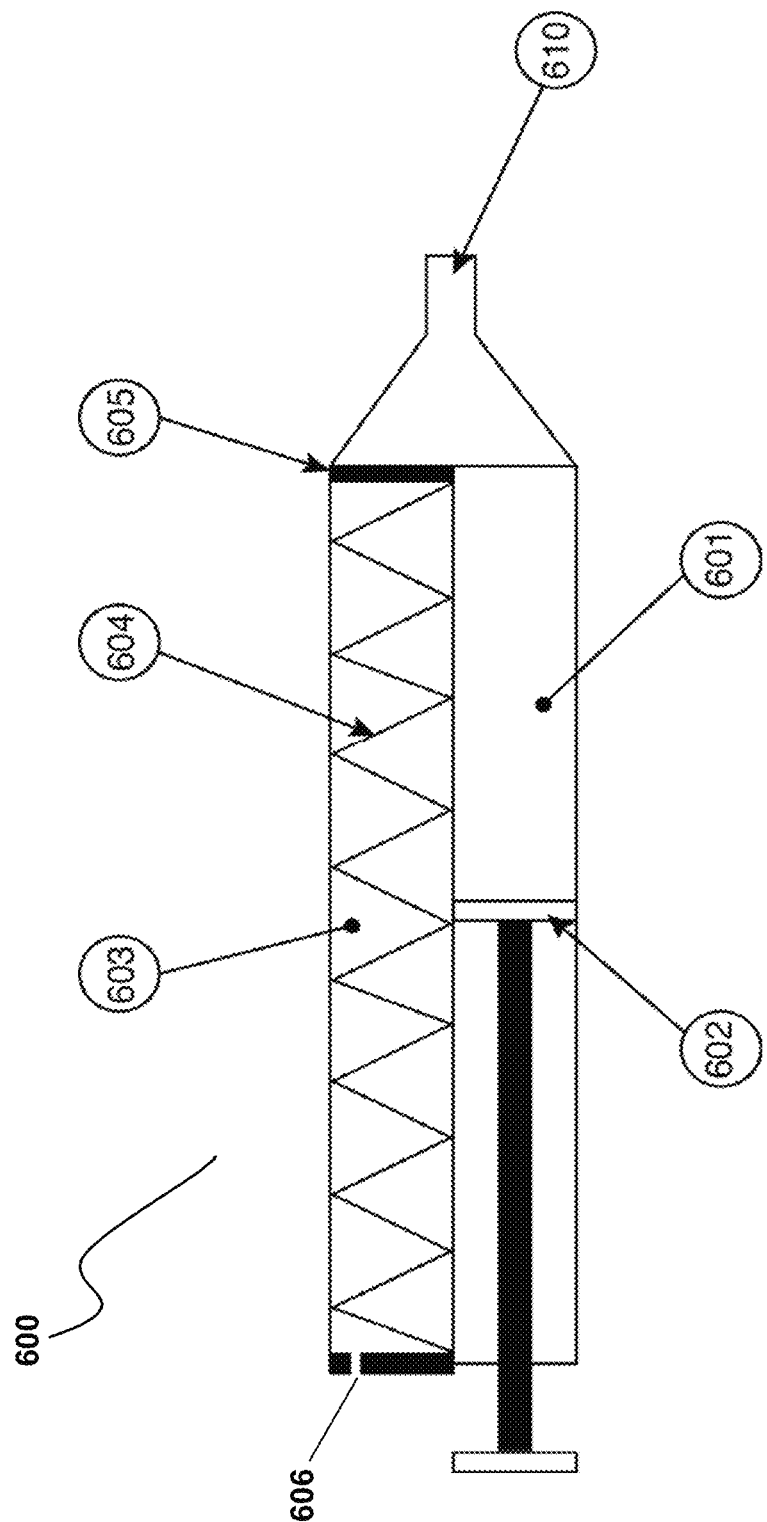
FIG. 6 shows an exemplary fluid pressure control device.

In a method of using a dual syringe fluid pressure control device 600 of FIG. 6, the operator fills syringe 601 as described for other devices herein, and controls plunger 602. With movement of plunger 602 toward exit port 610, fluid flows out exit port 610 until a fluid pressure is reached in the system. It is contemplated that exit port 610 is attached to a catheter. When there is back pressure on the fluid exiting the device, for example, from resistance to fluid flow from exit port 610, excess fluid is moved into the second container 603 which houses spring 604. In an aspect, the dual syringe device comprises a rubber seal 605 that prevents flow of a fluid until the extended spring pressure is overcome. The movable rubber seal functions similarly to indicating element 18 in FIG. 1 in that it moves in the cylinder, towards the operator, and pushes against the spring due to the pressure of the fluid. It does not allow fluid to pass into the spring chamber. The proximal vent allows the air in the chamber to move out so that there is no back pressure. When the spring has been moved by fluid and the operator stops, the spring advances the fluid by its force until it reseats the seal. The operator then begins again to inject fluid until the spring starts compressing again, thereby confirming that the pressure is such that the spring is moved. The force may be factored into the proper spring constant to give the final desired pressure. The vent serves as an assurance that pressure is not built behind the seal in the spring chamber portion of the left syringe. In use, the operator advances the plunger and upon reaching the desired pressure, the motion of the spring can be visualized as it retracts to balance the system pressure. The device uses spring tension and dual barrel features.

In an aspect, the present invention comprises a check-valve fluid pressure control device 700. In an aspect, the check-valve fluid pressure control device comprises a telescopic syringe design with an outer syringe 701, and an inner syringe 702 fitted with a seal 703 having an umbrella-style check valve 704. Inner syringe 702 may have an air vent opening 711 to allow exiting of air when inner syringe 702 is slidably moved from a proximal to distal location, or from a distal location to a proximal location within outer syringe 701. A distal location is nearer exit port 710. Inner syringe 702 is hollow and the cavity provides a container area 705 for fluid that enters when the predetermined fluid pressure is exceeded and check valve 704 opens. Appropriate valves for use in this aspect of the check-valve syringe system are available from commercial suppliers. The check valve may be made from known elastomers that provide the degree of hardness to provide predetermined pressure control. Fluid relief openings 704a and 704b allow entry of fluid into container area 705 of inner syringe 702. In use, inner syringe 702 acts like a plunger in a syringe, to move fluid contained by outer syringe 701 out of outer syringe 701 through exit port 710. When there is back pressure on the fluid exiting device 700, for example, from resistance to fluid flow from exit port 710, the fluid pressure opens check valve 704 and fluid is moved into syringe 702 through fluid relief entrances 704a and 704b. Illustrative examples of the check-valves and inner cylinder configurations are shown in FIGS. 8, 9, 10 and 11, where in FIG. 10, o-ring 101 may be present in inner syringe 702, and in FIG. 11, inner syringe 702 is shown with a flexible fluid seal 1101, that forms a small cavity 1102, into which fluid flows through opening 1103. When there is back pressure on the fluid exiting device 700, for example, from resistance to fluid flow from exit port 710, the fluid pressure opens check valve 704 and fluid is moved into container area 705 of inner syringe 702 through relief entrances 704a and 704b (not shown in FIG. 11). In an aspect, the check-valve syringe device may comprise a primary central mounting hole for the umbrella check valve and secondary vent openings under the umbrella. In an aspect, an inner syringe 702 may be filled with absorbent materials in container area 705. Such absorbent materials may be capable of displaying the entering fluid by wetting or color change by the absorbent material. In general, check-valve fluid pressure control device of the invention uses two concentric syringes, 701 and 702, with the inner syringe 702 having a sealing/check valve head.

In an aspect, the check-valve syringe device may comprise umbrella check valves shown in Table 1. These exemplary umbrella check valves can be obtained from commercial sources. Other umbrella check valves are known to one skilled in the art and can be used satisfactorily in place of those described in Table 1. The cited values in Table 1 are dependent on the cross-section of the seat base for the valve. An umbrella check valve may be manufactured from EPDM elastomers. In a further aspect, the umbrella check valve may be manufactured from Nitrile. Other materials that would function as a check valve in the present invention are known to those skilled in the art and are contemplated by the present invention.

TABLE 1

| Material | | Opening Pressure (mbar/mmHg) |
|---|---|---|
| VL1719Z33 | EPDM | 176/132 |
| VL1001M12 | Silicone | 321/not calculated |
| VL29Z49 | Nitrile | 822/not calculated |
| VL1001M14 | Silicone | 405/not calculated |
| VL1401M229 | Fluorsilicone | 163/122 |
| VL1001P74 | Silicone | 486/not calculated |

It is to be understood that the invention is not limited to specific synthetic materials unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

Definitions

As used in the specification and the appended claims, the singular forms "a," "an" and "the" include plural referents unless the context clearly dictates otherwise. Thus, for example, reference to "a fallopian tube," includes a plurality of two or more such anatomical structures and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Example 1: Fluid Pressure Control Device

A fluid pressure control device was constructed of components comprising a 10 mL syringe with male luer slip tip, a 10 mL syringe barrel with male luer lock tip, a flexible rubber diaphragm (Femasys P/N 330-009) with a maximum outer diameter appropriate to traverse the inner diameter of the 10 mL syringe barrel, a 3.0 PSI pressure relief valve with a female luer inlet port, a male luer slip outlet port, a 5.5 mm relief port (Femasys P/N 330-007), a elbow connector with two female ports (Femasys P/N 330-005), 0.8 inches of tubing (Femasys P/N 330-006), a one-way stopcock body (Femasys P/N 330-002), and a one-way stopcock handle (Femasys P/N 330-001). The internal components were contained within housing components comprising a top housing (Femasys P/N 330-013), a bottom housing (Femasys P/N 330-014), and two plunger knobs (Femasys P/N 330-012). The components were assembled as generally shown and described in FIG. 1.

Figure 12:
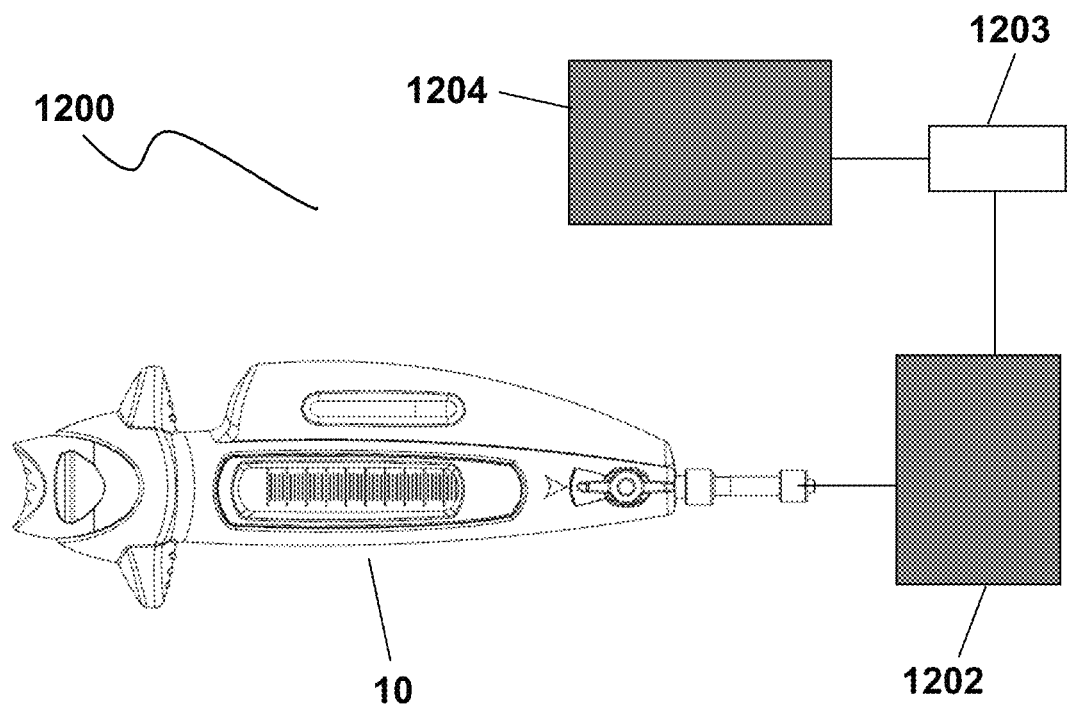
FIG. 12 shows a system for measuring fluid pressure from an exemplary device of the present invention.

A system 1200 for testing fluid pressure control device 10 was constructed comprising a disposable pressure transducer 1202 (Utah Medical P/N DPT-100), a pressure monitor 1203 (PendoTech PressureMat 3Plus), and a standard digital computer 1204. The components were assembled as generally shown in FIG. 12.

The fluid pressure control device and system of this example was designed to limit the injection pressure of fluid instilled into a closed system to a value at or below 200 mm Hg or other pressure as selected as being applicable for the targeted application. The fluid pressure control device 10 comprised a pressure relief valve positioned inline with a 10 mL syringe in this example. Fluid was injected via the manual actuation of the plunger knob. The fluid then passed through a pressure relief assembly, and if the inline pressure of the main through-port of the pressure relief assembly met or exceeded its pressure rating (3.0 PSI), the pressure relief valve opened, and fluid was directed into the 10 mL collection syringe barrel. To facilitate containment of the fluid expelled from the relief port of the pressure relief apparatus, the collection syringe barrel contained a diaphragm that traverses the length of the barrel along its inner diameter as the 10 mL syringe barrel fills.

Figure 13:
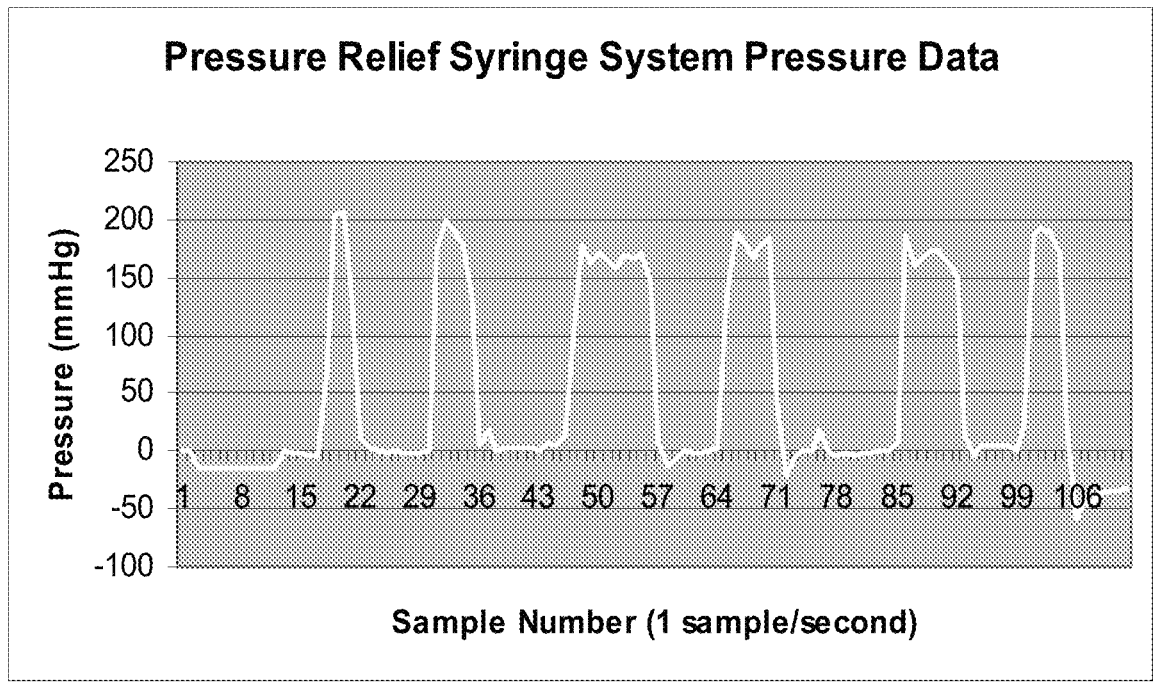
FIG. 13 shows data generated in measuring fluid pressure from an exemplary device of the present invention.

Fluid injection pressure measurements of the device in a closed system were obtained as follows: radiopaque contrast media (Bracco Diagnostic's ISO-VUE 370) was injected through the device, and a pressure transducer was placed inline to and downstream from the outlet port of the fluid pressure control system with a cap placed over the port on the opposite end of the transducer, creating a closed system. In order to ensure accurate fluid pressure readings, the transducer was primed with the contrast media, and it was visually verified that no air bubbles were in proximity of the sensing portion of the transducer before pressure measurements were obtained. 10 mL of contrast media were injected through the device, and pressure measurements were obtained. The test was repeated 6 times. Typical data are shown in FIG. 13.

The duration/width of the 6 pressure curves illustrated the various range of force exerted on the plunger of the 10 mL syringe, which directly related to varying fluid flow rates from the outlet port of the pressure relief assembly. At higher flow rates, the maximum injection pressure measured at the outlet port of the pressure relief syringe can exceed 200 mmHg.

Example 2: Pressure Relief Syringe System with Pressure Equalizer

Figure 14:
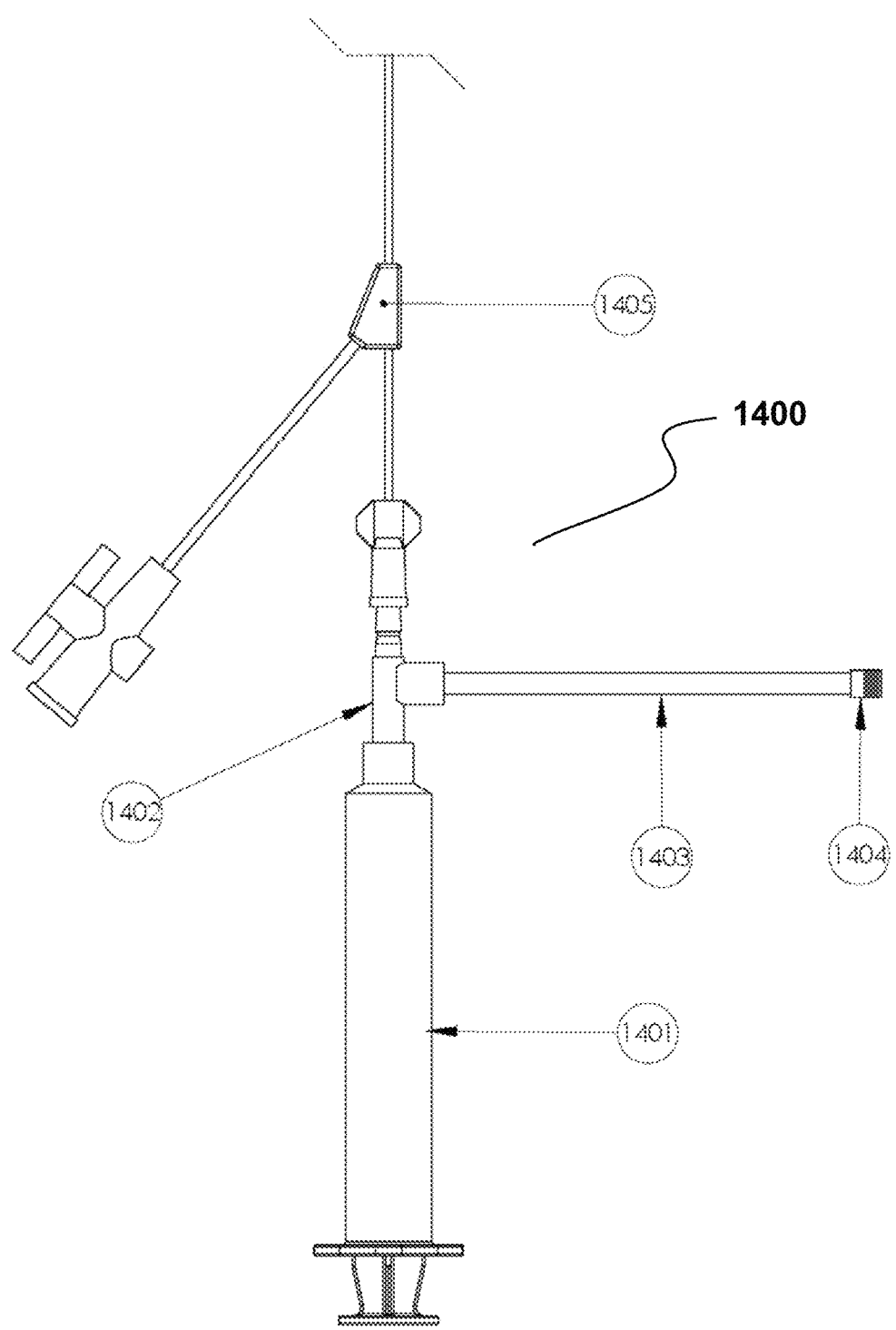
FIG. 14 shows an exemplary fluid pressure control device.

A fluid pressure control device similar to that described in Example 1 was adapted to add a pressure equalizer as shown in FIG. 14. First container 1401 is a 10 mL syringe, T-fitting 1402 is in fluid connection with first container 1401, a pressure equalizer 1403 is in fluid connection and is dimensioned so that the fluid path to the subjected container (organ, cavity or a conduit) and the line to the check valve both have similar outlet pressures. It can be modified using the Poiseuielle equation to predictably get these dimensions, and check valve 1404 is positioned as shown, with a particular pressure rating, for example 200 mm Hg. The device is attached to catheter 1405. The testing configuration is similar to actual use in that the fluid pressure control device advances contrast or fluid to a standard intrauterine catheter (5 fr size was used for this example) and ultimately into a patient.

Figure 15:
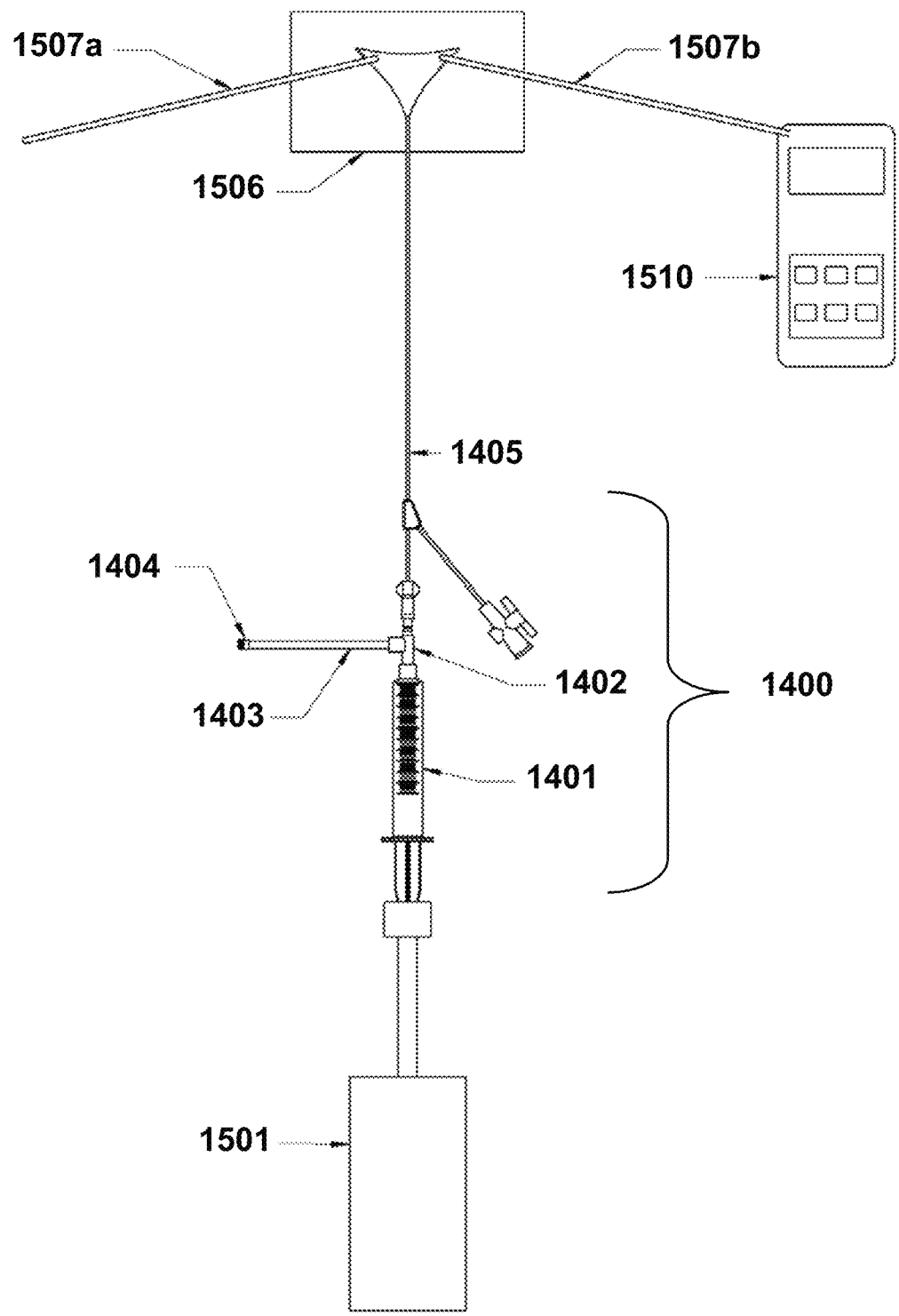
FIG. 15 shows a system for measuring fluid pressure from an exemplary device of the present invention.

To evaluate the effect of adding a pressure equalizer to the pressure relief syringe system; the entire unit was mounted on a table model force tester 1501 (i.e. Instron) to allow for the syringe plunger to be controllably advanced to deliver contrast medium at a fixed rate (see FIG. 15). The Instron 1501 was positioned horizontally on the laboratory bench and two rates were chosen to deliver reasonable and expected flows of 2 inches/minute (0.14 cc/second) and 5 inches/minute (0.35 cc/second). A simulated uterine model 1506 was used that incorporated fallopian tube lines 1507a/b of a diameter (2 mm) that is seen in a human female's fallopian tubes. One fallopian tube line 1507b was connected to the pressure gauge 1510 to obtain pressure relief measurements. The other fallopian tube line 1507a was occluded to allow for a closed system.

Table 2 below highlights the Poiseuille Law, which factors in the effects of viscosity, distance, and internal diameter of a conduit on a fluid flowing in a conduit. The check valve provided a mechanism to inform the operator that the device had applied the proper pressure to the structure being assessed. The Poiseuille effect predicts that as the distance and diameter changes, so does the perceived pressure. In other words, the greater the length and the smaller the diameter, the lower the actual pressure sensed will be in the assessed structure. The check valve registered the maximum pressure at its position in the device. Going distally towards the exit port, the pressure at that leading fluid point began to drop such that if long enough, the pressure could drop to zero and the operator would think the device has presented the appropriate pressure to the structure. In order to get a true equivalence of exit pressure and check valve performance, the check valve matched the pressure drop exhibited by the delivering conduit. This can accomplished either be by length or inner diameter or combinations of these dimensions in the conduit attached to the check valve.

As the examples in Table 2 below show, an increase in the flow rate of the fluid resulted in an increase in the uterine model pressure. This was evident in examples 3, 4, and 5 below which had no pressure equalizer; the check valve was incorporated directly into the t-fitting. This configuration displayed the safe aspects of having latitude in rates of delivery, yet be well under the check valve relief pressure. In comparing example 4 and 11, it was possible to observe a rise in uterine model pressure from 120 mmHg to 130 mmHg when the viscosity was increased from water at 1 cPs to a soap solution of 8.3 cPs at the same rate of delivery 0.35 cc/sec.

The examples are intended to show how one can modify the various dimensions and fluid viscosity to have agreement of sensed pressures. The examples do not show the case where both the uterine model pressure matches the check valve, but again the point was to show that by proper choice of variables, one can have such agreement at both locations.

plunger of a 10 mL syringe. The example device was constructed to limit pressure to below 200 mm Hg. Operationally, the fluid was drawn up into the device manually by pulling back on the trigger that is physically attached to the plunger of the 10 mL syringe. When the plunger is released, the trigger exerted a constant and known force on the syringe plunger via the pull force of two constant force springs requiring no user exerted force (see FIG. 5 and description herein). Because the force exerted on the syringe plunger was constant, fluid injection into a closed system was halted when the pressure of the system meets the pressure that correlates to the force exerted on the syringe plunger by the trigger/spring configuration. Thus, in a closed system, the injection pressure of the device can be maintained at the constant pressure that correlates to the force exerted on the syringe plunger by the trigger/spring configuration.

In order to obtain simulated fluid injection pressure measurements in a closed system, a distended balloon (obtained from the Sorin Bonchek Vein Distention System) was positioned in-line with a pressure transducer, and a closed one-way stopcock was attached to the opposite end of the transducer. See FIG. 16. The Bonchek System utilizes the elastomeric properties of the distended balloon to deliver fluid at a constant and known pressure requiring no user

TABLE 2

| Example | Viscosity/fluid | Length of pressure equalizer | Inner diameter of pressure equalizer | Rate of Delivery | Pressure Relieved |
| --- | --- | --- | --- | --- | --- |
| 1 | 1 cPs/water | 10 cm | 0.020" | 0.14 cc/sec | 298 mmHg |
| 2 | 1 cPs/water | 4 cm | 0.020" | 0.14 cc/sec | 270 mmHg |
| 3 | 1 cPs/water | NA | NA | 0.14 cc/sec | 110 mmHg |
| 4 | 1 cPs/water | NA | NA | 0.35 cc/sec | 120 mmHg |
| 5 | 1 cPs/water | NA | NA | 0.70 cc/sec | 140 mmHg |
| 6 | 1 cPs/water | 0.5" | 27 gauge | 0.35 cc/sec | 1,700 mmHg |
| 7 | 1 cPs/water | 0.5" | 27 gauge | 0.70 cc/sec | 1,800 mmHg |
| 8 | 1 cPs/water | 1.5" | 18 gauge | 0.35 cc/sec | 156 mmHg |
| 9 | 1 cPs/water | 1.5" | 18 gauge | 0.14 cc/sec | 140 mmHg |
| 10 | 300 cPs/Liquid soap | 1.5" | 18 gauge | 0.35 cc/sec | None - all escapes through valve |
| 11 | 8.3 cPs/liquid soap | NA | NA | 0.35 cc/sec | 130 mmHg |
| 12 | 8.3 cPs/liquid soap | 1.5" | 18 gauge | 0.14 cc/sec | 146 mmHg |
| 13 | 8.3 cPs/liquid soap | 1.5" | 18 gauge | 0.35 cc/sec | 186 mmHg |
| 14 | 33 cPs/liquid soap | 1.5" | 18 gauge | 0.14 cc/sec | 240 mmHg |
| 15 | 33 cPs/liquid soap | 1.5" | 18 gauge | 0.35 cc/sec | 290 mmHg |

Example 3: Control Delivery Mechanism with Constant Force Spring Design

Figure 5:
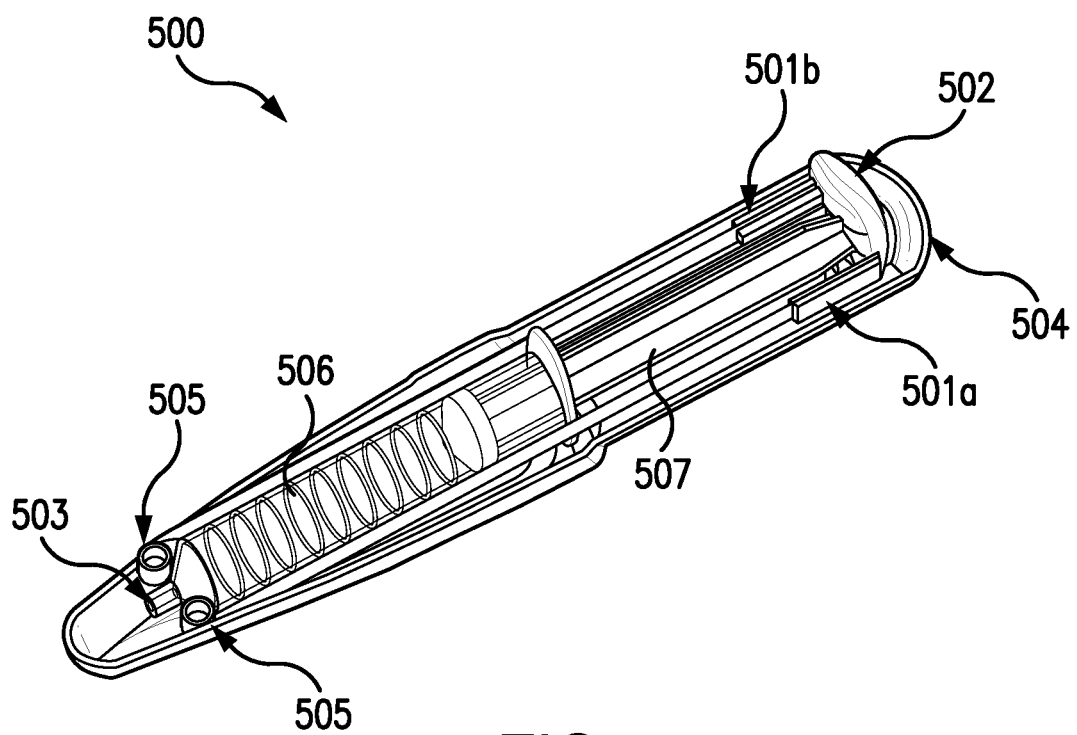
FIG. 5 shows an exemplary fluid pressure control device.

A fluid pressure control device with constant force spring was constructed comprising a 10 mL syringe with male Luer slip tip, two constant force springs, and a trigger for syringe plunger, as shown in FIG. 5. A data simulation system was constructed comprising three one-way stopcocks (Merit Medical P/N S1LFP), a balloon component of the Sorin Bonchek Vein Distention System 200 mmHg (Ref Number BSVD-200), and a 60 cc syringe component of the Sorin Bonchek Vein Distention System 200 mmHg (Ref Number BSVD-200). A pressure measuring system was constructed comprising a disposable pressure transducer (Utah Medical P/N DPT-100), a pressure monitor (PendoTech PressureMat 3Plus), and a standard digital computer. The assembling of these components is shown in FIG. 16.

The fluid pressure control device with constant force spring was designed to limit the injection pressure of fluid dispensed into a closed system to below a targeted value by incorporating a constant force trigger that interfaces with the exerted force. In a manner similar to that described in this example, fluid injection into a closed system was halted when the pressure in the system meets the injection pressure that correlates to the force exerted by the balloon's elastomeric properties. Thus, in the simulated setup for this example, the injection pressure in a closed system can be maintained at the constant pressure that correlates to the force exerted on the fluid by the balloon.

Figure 16:
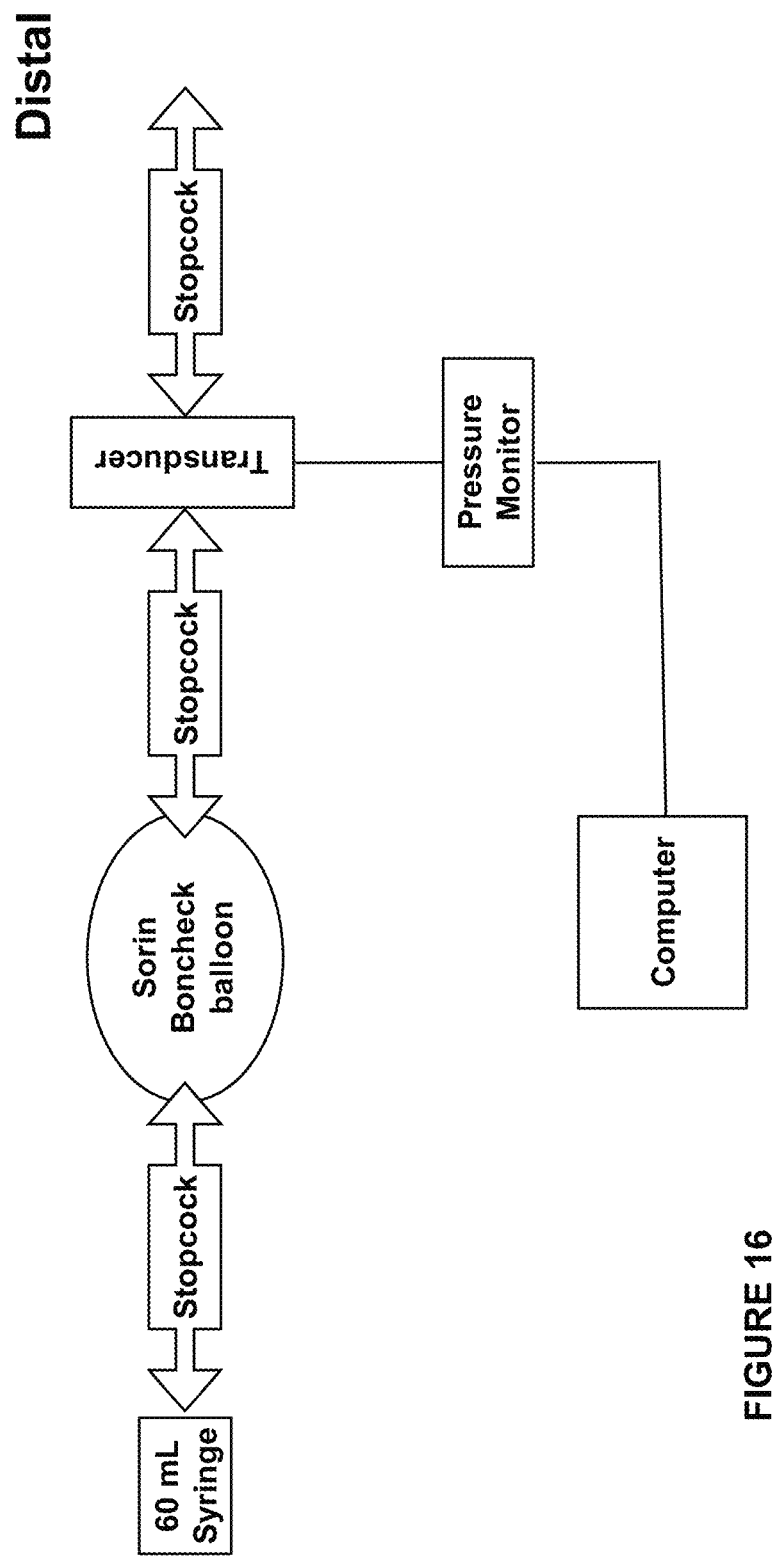
FIG. 16 shows a schematic of a system for measuring fluid pressure from an exemplary device of the present invention.

All of the stopcocks were in the open position, the system depicted in FIG. 16 was primed with saline until the balloon was filled, but not distended, and the transducer had no visible air bubbles in proximity to its sensor. After priming, the stopcock at the distal portion of the setup was maintained in a closed position. To distend the balloon, the stopcock positioned between the transducer and the balloon was closed, and 20 mL of saline was injected into the balloon using a 60 mL syringe. After the balloon was distended, the stopcock between the 60 mL syringe and the balloon was closed, the stopcock between the transducer and the balloon was opened, and pressure measurements were recorded.

Figure 17:
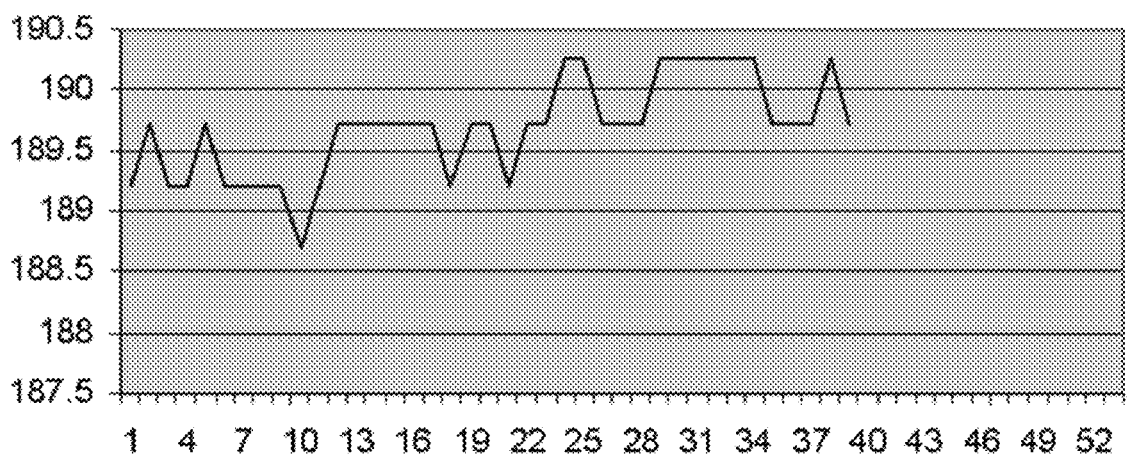
FIG. 17 shows data generated in measuring fluid pressure from an exemplary device of the present invention.

The data presented in FIG. 17 illustrated that the injection pressure of the setup in a closed system was maintained at a value below 200 mmHg, and the injection pressure was constant within 2 mm Hg.

An embodiment of a device used in this example comprised an ABC Syringe Infusion Pump (Elixir), a Crono S-Pid 50, and other syringe pumps as determined to be applicable to this use. Infusion pumps were more desirable than Sorin vein distension system and related devices due to intended use, anatomical area, and principle of operation.

Example 4: Check Valve Syringe System

A check-valve fluid pressure control device comprising a 12 cc Monoject syringe plunger tip with the tip bored centrally and off-center (for fluid release) to allow mounting of an umbrella check valve such as the Verney VL2491-102 and VL1195-102. A check-valve syringe system may comprise a Delrin solid rod plunger sized so as to be able to fit into the 12 cc Monject syringe barrel. Other syringes and plungers can be used, including 3 cc to 12 cc. Larger sizes can be implemented as required by the particular application. The particular check valve is determined by the desired pressure limit. In this example, the check-valve limits pressure to just under the 200 mm Hg limit.

Figure 7:
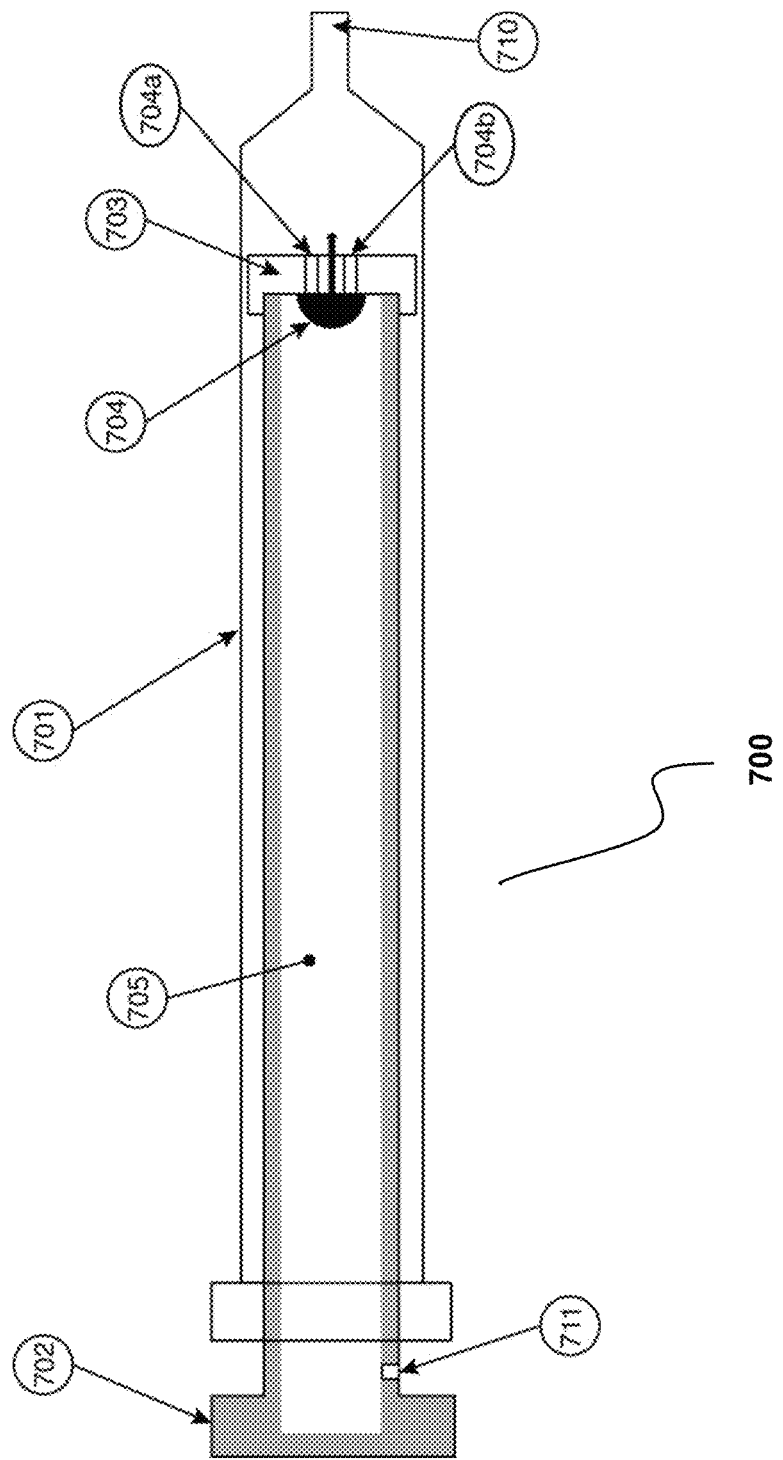
FIG. 7 shows an exemplary fluid pressure control device.
Figure 8:
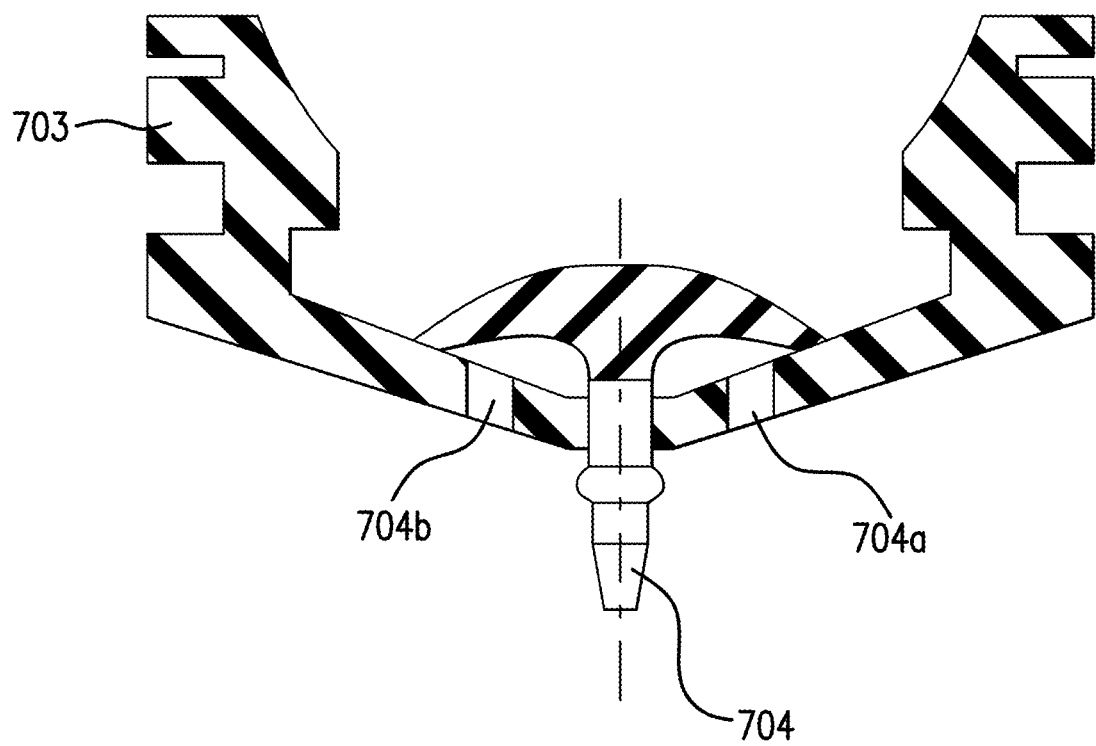
FIG. 8 shows an exemplary umbrella style check valve.
Figure 9A:
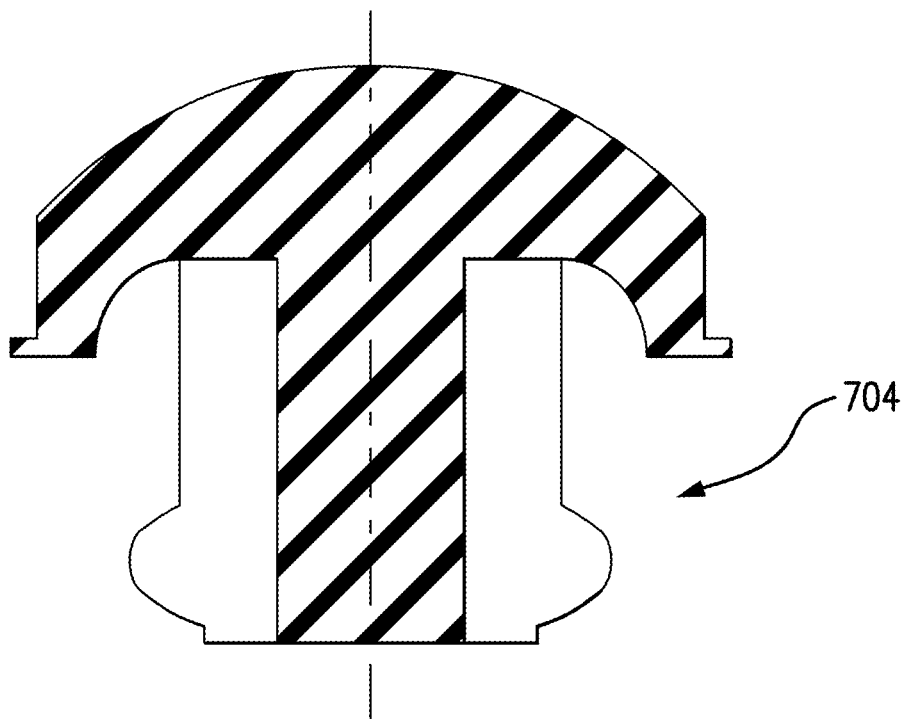
FIGS. 9A and 9B each show an exemplary umbrella style check valve.
Figure 9B:
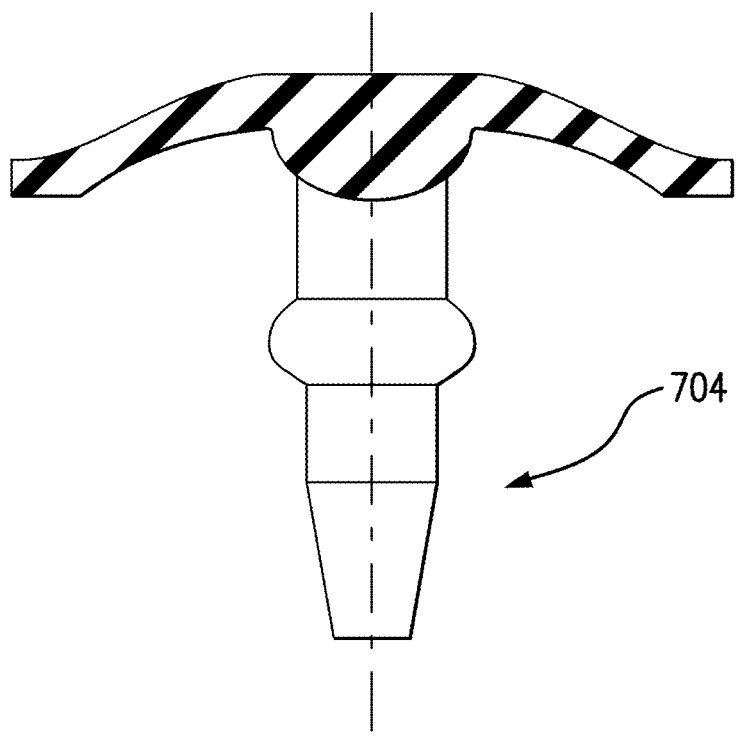

An example of a check-valve fluid pressure control device is shown in FIG. 7. The syringe barrel has a central mounting hole for the umbrella check valve, with one or more secondary venting holes located beneath the umbrella check valve. Once the fluid pressure dispensed from the outer syringe exceeded the release pressure of the umbrella check valve, the fluid would flow into the inner syringe. The inner syringe, as determined by the requirements of the end use, can be fitted with absorbent materials capable of displaying the fluid by wetting or alternatively undergo a color change within the inner syringe upon wetting by the fluid.

Umbrella check valves suitable for use in the check-valve syringe system are given in Table 3 (see above; materials and dimensional information on the umbrella check valves shown in Table 1). Additional umbrella check valves suitable for use in the check valve fluid pressure control device are given below in Table 3.

TABLE 3

Umbrella check valves.

| Part No. | | Material | Opening Pressure (mbar/mmHg) |
|---|---|---|---|
| VL237-106 | VL1401M247 | Fluorosilicone | 37.4/not calculated |
| VL1195-102 | VL1704Z6 | EPDM | 122/94 |
| VL2491-102 | VL115X61 | Nitrile | 114/98 |
| VL2601-102 | VL1001M12 | Silicone | 39.5/not calculated |
| VL4544-102 | VL1001P61 | Silicone | 20.6/not calculated |

Figure 10:
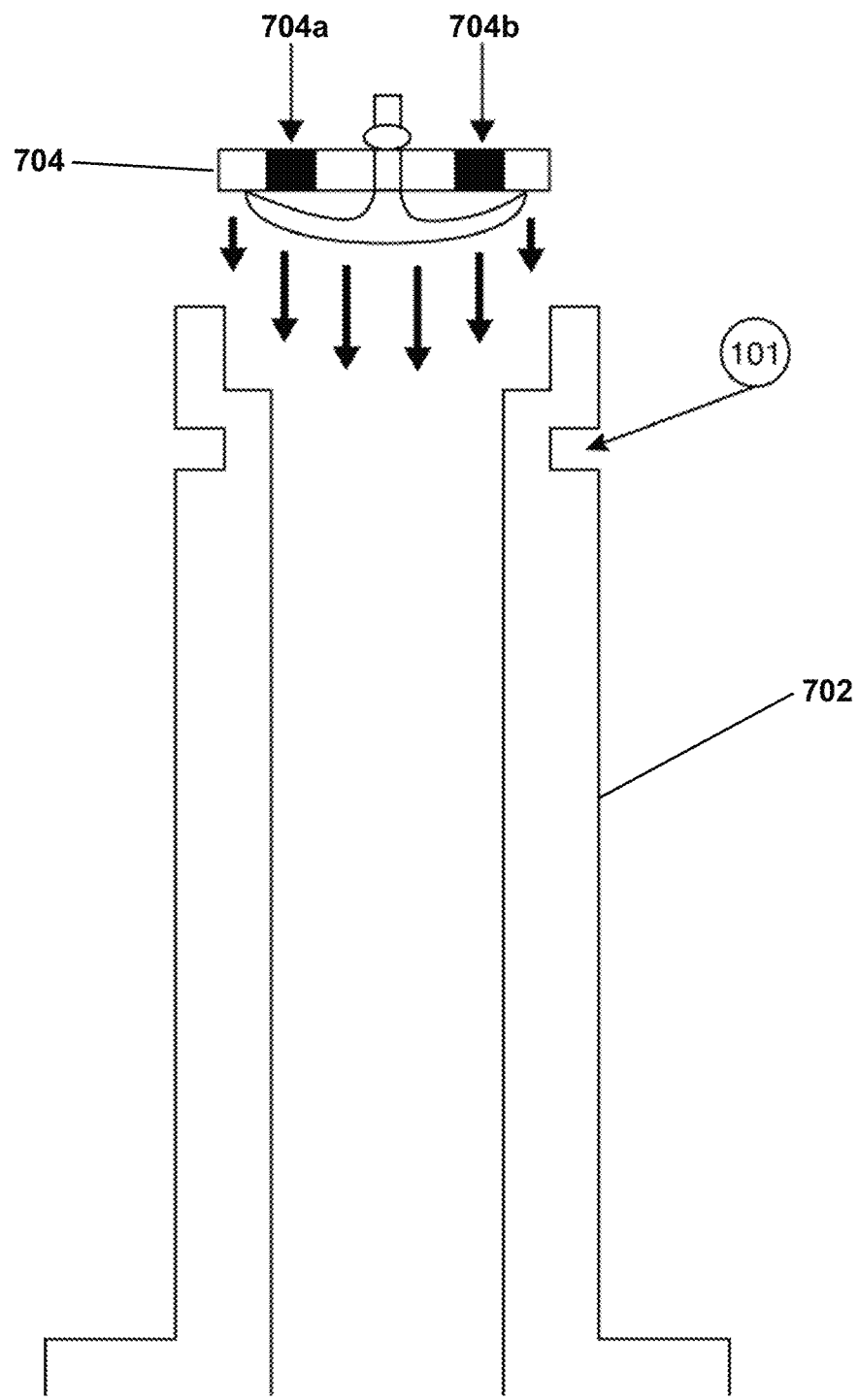
FIG. 10 shows detail of an exemplary fluid pressure control device.

In this example, the rubber septum that is found on the end of a syringe plunger was modified so that it contains an umbrella check valve. The syringe plunger was further modified to have at least one fluid vent hole. The rubber septum thus modified is fit onto a hollow barrel tube that replaces the normal syringe barrel. The hollow barrel can optional be fitted with an external o-ring to insure a fluid-tight seal with the outer syringe as depicted in FIG. 10. The container area 705 acts as a fluid capture chamber upon release of the umbrella check valve.

Figure 11:
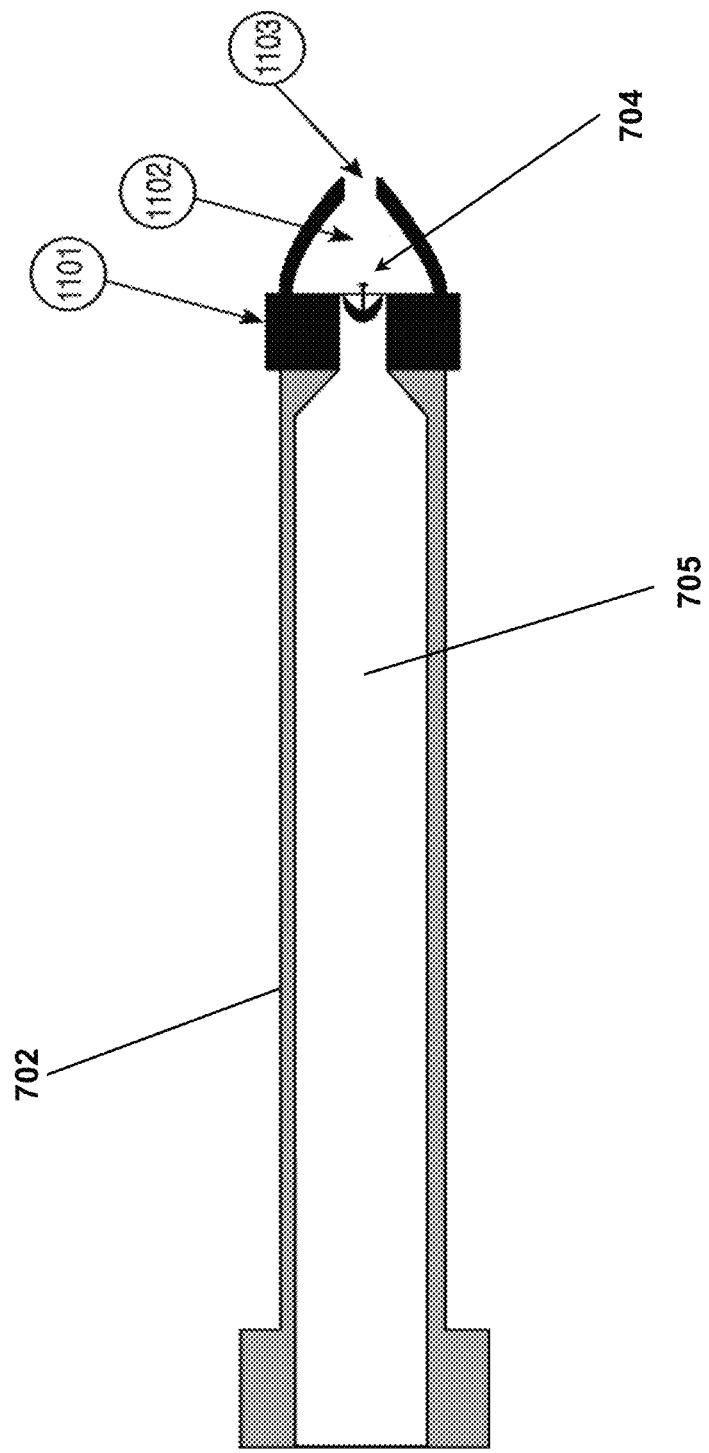
FIG. 11 shows detail of an exemplary fluid pressure control device.

An example of a check-valve fluid pressure control device is shown in FIG. 11. In this example, the rubber septum as described above is replaced by a solid, circular, bio-compatible end pieced fabricated from solid, sheet stock (e.g. polyethylene, nylon, polyester, polycarbonate, or other appropriate polymers), or molded from such polymers, and dimensioned to fit the end of a hollow barrel tube. The end piece comprises at least one vent hole and a hole to accept the umbrella check valve. It is then pressed into the hollow barrel such that the pressure relief action can be performed without fowling against the barrel recess. An o-ring may be needed in this example to provide a seal against the outer barrel to which this assembly is inserted. This hollow barrel can optionally be constructed of soft polymers, like olefins, and fitted with a slight lip instead of the o-ring slot to provide the necessary seal against the outer barrel.

An approach utilized as much of the 12 cc syringe as possible and so the rubber plunger was removed to allow for the re-shaping of the plunger rod so that the conic tip is absent and a central bore is made to allow for the released fluid to pass towards the operator. The rubber plunger was modified and re-fitted to the modified plunger rod. This variant had the plunger rod proximally fitted with absorbent material for visualization as well as keeping the user from contact with released fluid, thereby providing a set of values that appear desirable for the region of interest.

A syringe with a combination check valve was tested, having a single vent point that also acts as the retainer of the check valve. The pressure readings were lower than that of the other check valve versions described above.

An example of a fitting for a syringe plunger is shown in FIG. 11. This fitting can be fabricated from the appropriate elastomeric material, including, for example, Delrin. The fitting shown is dimensioned for a 3 cc syringe, but can be appropriately modified and scaled for other syringe types.

Figure 18:
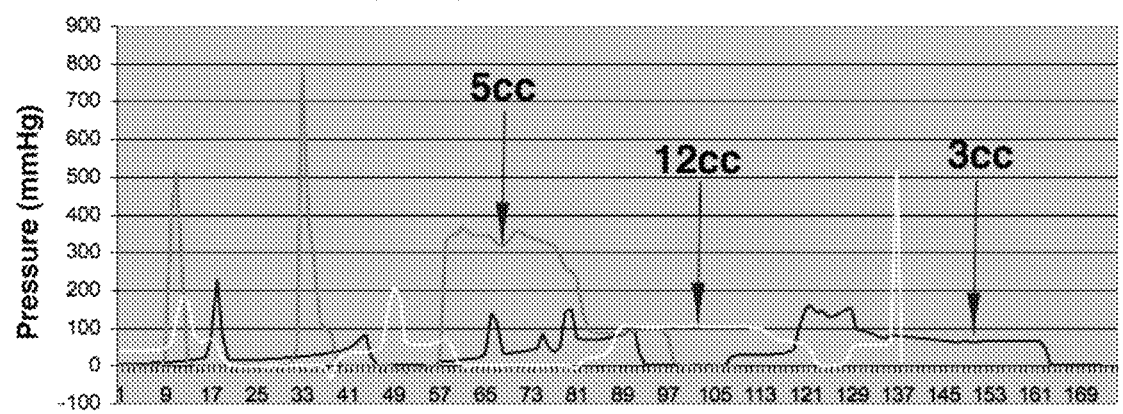
FIG. 18 shows data generated in measuring fluid pressure from an exemplary device of the present invention
Figure 19:
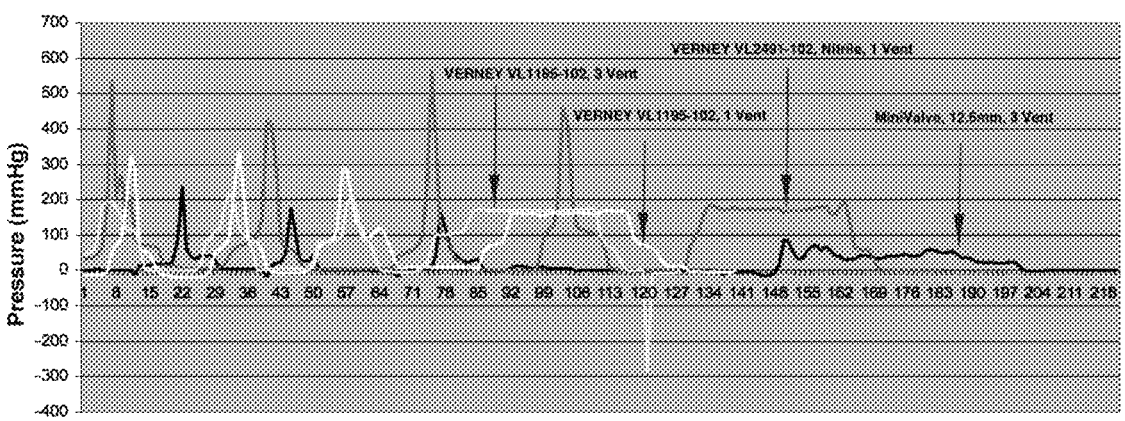
FIG. 19 shows data generated in measuring fluid pressure from an exemplary device of the present invention.

Check valve fluid pressure control device pressure profiles are shown in FIGS. 18 and 19.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for pressure-regulated imaging of a patient comprising,
    a) administering to a patient an imaging fluid, and imaging at least a portion of at least one fallopian tube or uterus, or both, of the patient, the imaging fluid created and delivered under pressure control by a device comprising,
        (i) a first syringe for fluid, and a second syringe for air, each in fluid connection with an exit port comprising attachment elements, and each syringe having a plunger slidably disposed therein, and configured to be moved simultaneously;
        (ii) a pressure relief valve having a proximal port, a distal port and a lateral port, wherein the pressure relief valve is in fluid connection between the exit port comprising the attachment elements and the syringes, and wherein the pressure relief valve is configured to move from a closed state to an open state at a predetermined fluid pressure; and
            wherein when the plungers are simultaneously moved proximally, the device is configured to take a fluid into the device through the exit port comprising the attachment elements and into the first syringe and air into the second syringe, and wherein, when the plungers are simultaneously moved distally, the device is configured to create and deliver an imaging fluid comprising a mixture of the fluid and air through the exit port comprising the attachment elements;

wherein at least one fallopian tube or uterus, or both, of the patient have an altered physical structure; and wherein administering the imaging fluid comprises the steps of:

b) after contacting the exit port comprising the attachment elements to a fluid, proximally moving simultaneously the two plungers to fill the first syringe with the fluid entering through the exit port comprising the attachment elements, and the second syringe with air;

c) attaching the exit port comprising the attachment elements to a proximal end of a catheter;

d) positioning the catheter's distal end at a target site of the at least one fallopian tube or uterus;

e) sliding simultaneously the two plungers distally to move the fluid and air from the respective syringes and to mix the fluid and air to form the imaging fluid that is delivered at or near the target site of the at least one fallopian tube or uterus, and wherein the imaging fluid is delivered to the at least a portion of at least one fallopian tube or uterus or both at or below the predetermined pressure; and if the imaging fluid reaches the predetermined pressure, the pressure relief valve opens, and the imaging fluid exits through the relief valve.

2. The method of claim 1, wherein the catheter is a uterine access catheter having a balloon near the distal end of the catheter for maintaining an imaging fluid in the uterus.

3. The method of claim 1, further comprising the step of viewing the imaging fluid in at least the proximal portion of the at least one fallopian tube or uterus or both.

4. The method of claim 3, wherein the imaging fluid is viewed with sonography.

5. The method of claim 1, wherein the imaging fluid further comprises a treatment fluid.

6. The method of claim 1, wherein the uterus having an altered physical structure has undergone one or more of a surgical procedure, a medical procedure, or a trauma that has changed the physical structure of the uterus.

7. The method of claim 1, wherein the at least one fallopian tube having an altered physical structure has undergone one or more of a surgical procedure, a medical procedure, or a trauma that has changed the physical structure of the at least one fallopian tube.

8. The method of claim 1, wherein the uterus and the at least one fallopian tube having an altered physical structures have undergone one or more of a surgical procedure, a medical procedure, or a trauma that has changed the physical structure of the at least one fallopian tube.

9. The method of claim 1, wherein the imaging fluid is delivered at least to the uterus.

10. The method of claim 9, wherein delivering the imaging fluid to the uterus further comprises delivering the imaging fluid to the at least a portion of at least one fallopian tube.

11. The method of claim 1, wherein the pressure relief valve is configured to move from a closed state to an open state at 200 mm Hg.

12. The method of claim 1, wherein the pressure relief valve is configured to move from a closed state to an open state at 150 mm Hg.

13. The method of claim 1, wherein the at least one fallopian tube has been occluded, blocked or severed.

14. The method of claim 1, further comprising moving a stopcock positioned between the pressure relief valve and the exit port comprising the attachment elements from an open configuration to a closed configuration to prevent the flow of fluid through the exit port when the fluid pressure reaches the predetermined fluid pressure.

15. A imaging fluid creation and delivery device comprising:

(i) a first syringe for fluid, and a second syringe for air each in fluid connection with an exit port comprising attachment elements, and each syringe having a plunger slidably disposed therein, and configured to be moved simultaneously;

(ii) a pressure relief valve having a proximal port, a distal port and a lateral port, wherein the pressure relief valve is in fluid connection between the exit port comprising the attachment elements and the syringes, and wherein the pressure relief valve is configured to move from a closed state to an open state at a predetermined fluid pressure of at least 150 mm Hg; and wherein when the plungers are simultaneously moved proximally, the device is configured to take a fluid into the device through the exit port comprising the attachment elements and into the first container and air into the second container, and wherein, when the plungers are simultaneously moved distally, the device is configured to create and deliver an imaging fluid comprising a mixture of the fluid and air through the exit port comprising the attachment elements.

16. The device of claim 15, further comprising a catheter attached to the exit port comprising the attachment elements.

17. The device of claim 15, wherein the pressure relief valve is configured to move from a closed state to an open state at 200 mm Hg.

18. The device of claim 15, wherein the pressure relief valve is configured to move from a closed state to an open state at 150 mm Hg.

19. The device of claim 15, wherein fluid pressure control device comprises a stopcock, having an open configuration and a closed configuration, positioned between the pressure relief valve and the exit port comprising the attachment elements.

* * * * *